US011529493B2

(12) United States Patent
Weiss et al.

(10) Patent No.: US 11,529,493 B2
(45) Date of Patent: Dec. 20, 2022

(54) MULTIFUNCTION SLEEP TRAINING DEVICE WITH REMOTE LOCKING MECHANISM AND METHODS OF OPERATION THEREOF

(71) Applicant: Hatch Baby, Inc., Menlo Park, CA (US)

(72) Inventors: David Weiss, Menlo Park, CA (US); Ann Crady Weiss, Menlo Park, CA (US); Stuart Tyrrell, Los Altos, CA (US); Jillian Locks, San Mateo, CA (US); Philip Bourgeois, Woodside, CA (US); George Turvey, Brookdale, CA (US); Martin Schnitzer, San Francisco, CA (US)

(73) Assignee: Hatch Baby, Inc., Palo Alto, CA (US)

( * ) Notice: Subject to any disclaimer, the term of this patent is extended or adjusted under 35 U.S.C. 154(b) by 134 days.

(21) Appl. No.: 16/708,256

(22) Filed: Dec. 9, 2019

(65) Prior Publication Data

US 2020/0125036 A1 Apr. 23, 2020

Related U.S. Application Data

(63) Continuation of application No. PCT/US2018/036942, filed on Jun. 11, 2018.
(Continued)

(51) Int. Cl.
*A61M 21/00* (2006.01)
*A61M 21/02* (2006.01)
(Continued)

(52) U.S. Cl.
CPC ............ *A61M 21/02* (2013.01); *G04C 23/08* (2013.01); *G04G 11/00* (2013.01); *G04G 13/025* (2013.01);
(Continued)

(58) Field of Classification Search
CPC .......... A61M 21/02; A61M 2021/0027; A61M 2021/0044; H05B 47/19; G04C 23/08;
(Continued)

(56) References Cited

U.S. PATENT DOCUMENTS 5,909,087 A 6/1999 Bryde et al.
6,236,622 B1 5/2001 Blackman
(Continued)

FOREIGN PATENT DOCUMENTS

CN 105889847 A * 8/2016 ............... F21S 9/02
EP 1886707 2/2008
(Continued)

OTHER PUBLICATIONS

Voch ("Night Light Bluetooth Speaker, Portable Wireless Bluetooth Speaker, 6 Color LED Themes Bedside Table Light/Smart Touch Control Color Changing Stereo Subwoofer" available at Amazon. com on Feb. 27, 2017, accessed online on Jun. 14, 2021) (Year: 2017).*

*Primary Examiner* — Kaylee R Wilson
(74) *Attorney, Agent, or Firm* — Levine Bagade Han LLP

(57) ABSTRACT

A sleep training device is disclosed comprising certain electronic components, audio components, light-emitting diodes (LEDs), physical switches, a capacitive touch component, or a combination thereof. The sleep training device can have a housing configured to house the electronic components, the audio components, the LEDs, the capacitive touch component, and at least part of the physical switches. The sleep training device can receive an instruction to schedule a sleep program based on a set parameter from another device in wireless communication with the sleep training device, initiate the sleep program once the set
(Continued)

parameter is met, and disable at least one of the physical switches and the capacitive touch component when the sleep program is initiated.

42 Claims, 19 Drawing Sheets

Related U.S. Application Data

(60) Provisional application No. 62/518,451, filed on Jun. 12, 2017.

(51) Int. Cl.
    *G04C 23/08*     (2006.01)
    *G04G 11/00*     (2006.01)
    *G04G 13/02*     (2006.01)
    *G08B 25/10*     (2006.01)
    *H05B 47/19*     (2020.01)

(52) U.S. Cl.
    CPC .............. *G08B 25/10* (2013.01); *H05B 47/19* (2020.01); *A61M 2021/0027* (2013.01); *A61M 2021/0044* (2013.01)

(58) Field of Classification Search
    CPC ...... G04C 19/02; G04G 11/00; G04G 13/025; G08B 25/10
    See application file for complete search history.

(56) References Cited

U.S. PATENT DOCUMENTS

| | | |
|---|---|---|
| 9,408,282 B1 | 8/2016 | Springer |
| 2003/0231778 A1 | 12/2003 | Landa |
| 2005/0248962 A1 | 11/2005 | Searfoss |
| 2007/0217290 A1 | 9/2007 | Rock |
| 2008/0225510 A1* | 9/2008 | Rocha ................. F21V 33/0056 362/86 |
| 2009/0034778 A1* | 2/2009 | Chi ........................ H04R 1/028 381/394 |
| 2009/0079561 A1* | 3/2009 | Nelson .................... G04C 11/00 340/540 |
| 2010/0067227 A1 | 3/2010 | Budike |
| 2010/0271802 A1* | 10/2010 | Recker ...................... H02J 3/00 362/20 |
| 2011/0301727 A1* | 12/2011 | Ansfield ................ G04G 13/02 700/94 |
| 2012/0188079 A1 | 7/2012 | Nelson |
| 2014/0018609 A1 | 1/2014 | Howard et al. |
| 2014/0223058 A1* | 8/2014 | Matsunaga ............. G06F 21/30 710/200 |
| 2014/0334653 A1 | 11/2014 | Luna et al. |
| 2014/0355246 A1* | 12/2014 | Yotsumoto ................ F21K 9/23 362/86 |
| 2015/0224417 A1 | 8/2015 | Richardson et al. |
| 2016/0023124 A1* | 1/2016 | Wang ...................... A63J 17/00 381/77 |
| 2016/0151603 A1 | 6/2016 | Shouldice et al. |
| 2016/0213308 A1 | 7/2016 | Proud |
| 2016/0231825 A1* | 8/2016 | Thijssen ................. G06F 3/017 |
| 2016/0323978 A1* | 11/2016 | Raza ...................... F21V 15/02 |

FOREIGN PATENT DOCUMENTS

| | | |
|---|---|---|
| GB | 2288687 | 10/1995 |
| WO | WO 2016/182714 | 11/2016 |
| WO | WO 2016/199101 | 12/2016 |
| WO | WO 2018/231720 | 12/2018 |

* cited by examiner

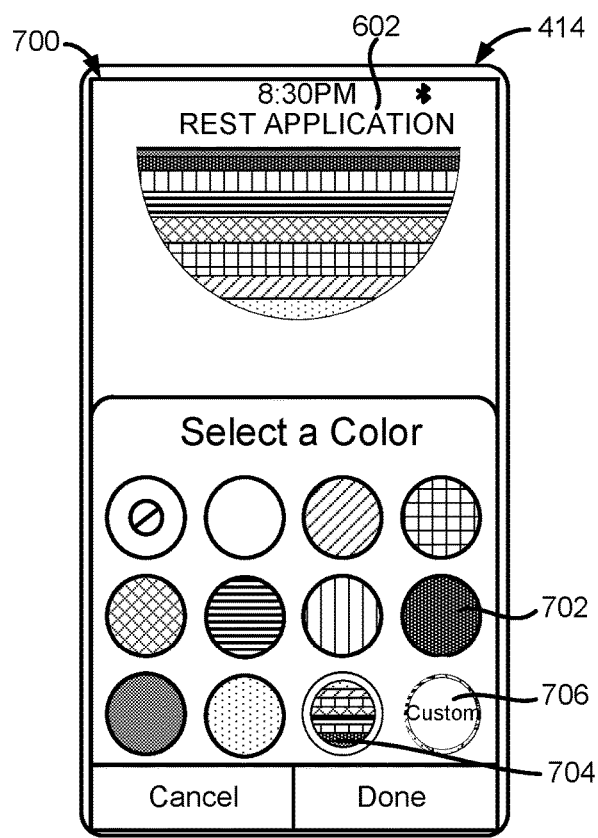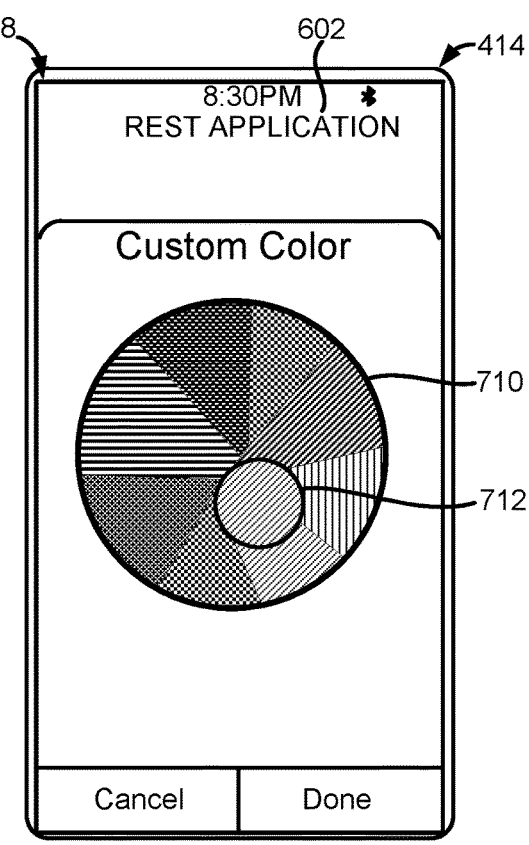
FIG. 7A  FIG. 7B

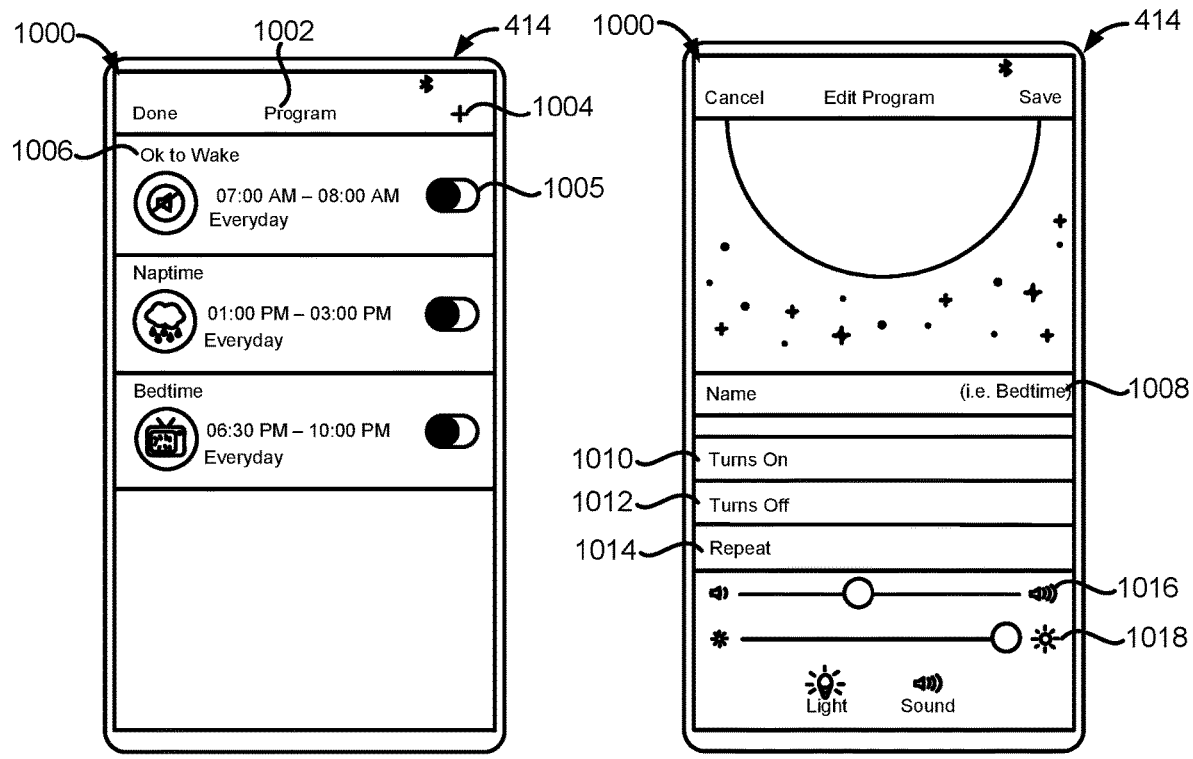
FIG. 10A  FIG. 10B
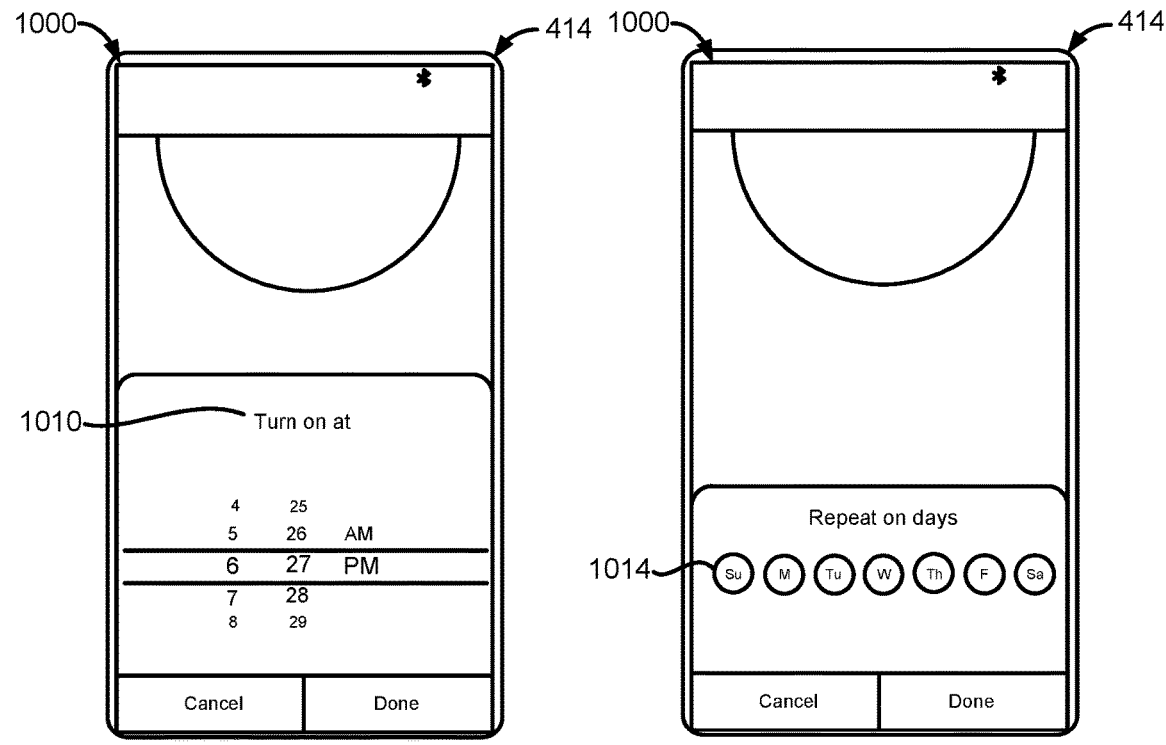
FIG. 10C  FIG. 10D

MULTIFUNCTION SLEEP TRAINING DEVICE WITH REMOTE LOCKING MECHANISM AND METHODS OF OPERATION THEREOF

CROSS-REFERENCE TO RELATED APPLICATIONS

This application is a continuation of International Patent Application No. PCT/US2018/036942, which claims the benefit of priority to U.S. Provisional Application No. 62/518,451, filed on Jun. 12, 2017, the contents of which are hereby incorporated by reference in their entireties.

FIELD OF TECHNOLOGY

The present disclosure relates generally to the field of infant or child sleep training devices, and, more specifically, to a multifunction sleep training device with a remote locking mechanism and methods of operation thereof.

BACKGROUND

Parents of young children often experience high levels of anxiety concerning their children's sleep habits. Researchers in the field of child development have noted that cognitive deficits and high hyperactivity were most strongly associated with a pattern of short sleep duration. See Touchette et al., *Associations Between Sleep Duration Patterns and Behavioral/Cognitive Functioning at School Entry*, Sleep (2007); 30(9): 1213-1219 and Dahl, Ronald E., *Sleep and the Developing Brain*, Sleep (2007); 30(9): 1079-1080.

One way to encourage healthy sleeping habits is by establishing a regular bedtime or naptime routine using visual and auditory cues generated by sleep training devices such as nightlights or white-noise machines, respectively. In addition, alarm clocks and lights for informing a child of the appropriate time to exit the child's room or bed have become popular for parents of toddlers eager to seek their parent's attention immediately upon the toddler's waking.

However, traditional nightlights, alarm clocks, and white-noise machines often must be controlled by manually-operated switches or buttons which require a parent to fumble with such controls in a dimly-lit room. In addition, parents often must program and set each device individually, which elongates a child's nighttime or naptime routine. Furthermore, such devices often take up valuable shelf space or table space on a child's nightstand or dresser. Also, a sleep deprived or distracted parent may forget to activate or set one or more sleep training devices, which may necessitate a parent having to return to the room and rouse a dozing child. Moreover, once a parent has successfully activated or programmed such a device and exited the child's room, the continued control of such a device is often dictated by the whims and impulses of a curious toddler or young child.

Therefore, a solution is needed that can assist parents with establishing healthy and regular sleeping routines by combining the beneficial features of multiple sleep training devices. In addition, such a solution should allow a parent to control the device remotely and schedule programs which automatically activate certain visual and auditory cues. Moreover, such a solution should allow the parent to remotely lock certain buttons or switches such that control of the device rests with the parent. Furthermore, the solution should not be overly complex and be cost-effective to manufacture.

SUMMARY

A multifunction sleep training device with a remote locking mechanism is disclosed. The sleep training device can include a printed circuit board (PCB) having a processor, a real-time clock integrated circuit (IC), a memory, a wireless communication unit, or a combination thereof coupled to the PCB. The sleeping training device can also include an audio component, light-emitting diodes (LEDs), and physical switches electrically coupled to the processor. The sleep training device can have a device housing configured to house the PCB, the audio component, the LEDs, and at least part of the physical switches.

The processor can be programmed to execute instructions stored in the memory to disable at least one of the physical switches when a sleep program stored in the memory is initiated. The sleep program can be initiated when a set parameter associated with the sleep program is met. The sleep program can be scheduled remotely using another device such as a client device or a voice-enabled assistance device. The sleep program can also be initiated when a user applies a user input to the client device or a user supplies a voice input to the voice-enabled assistance device and instructions concerning the sleep program are first transmitted to one or more servers in wireless communication with the sleep training device and the one or more servers transmits the instructions concerning the sleep program to the sleep training device.

The processor can further be programmed to receive a lock instruction from at least one of a client device and from a server in wireless communication with the sleep training device and disable at least one of the physical switches in response to the lock instruction received. The lock instruction can be transmitted initially by the client device upon a user applying a user input to a graphical user interface displayed on a display of the client device. The client device can transmit the lock instruction without requiring the user to initiate a sleep program. For example, a lock user interface can be rendered through a mobile application running on the client device. The lock user interface can be displayed as a standalone page of the mobile application or as part of another page. A user can apply a user input to a lock toggle displayed as part of the lock user interface to initiate a lock function and transmit the lock instruction directly to the sleep training device or to a server communicatively coupled to the sleep training device.

The device housing can include a housing base and a light diffusing cover. The PCB can be housed within the housing base. The light diffusing cover can be made of or comprise a polymeric material configured to diffuse light and dissipate heat generated by the LEDs. The sleep training device can also include a support column extending upward from the housing base. The support column can support at least part of the audio component and house one or more electrical components. The support column can also be covered by an opaque material such that the one or more electrical components within the support column do not cast shadows from light generated by the LEDs.

The LEDs can be arranged in a circular pattern surrounding the support column. The LEDs can include red-green-blue-and-white (RGBW) LEDs.

The audio component can include a speaker and an amplifier electrically coupled to the processor. The top of the device housing can be covered by a covering plate positioned about the speaker.

The sleep training device can also include a capacitive touch component. At least part of the capacitive touch component can be exposed by the device housing. For example, the capacitive touch component can be shaped as an annulus or ring surrounding the covering plate on the top of the device housing. The capacitive touch component can also include at least part of a covering plate used to cover the speaker. The capacitive touch component can be or comprise a stainless steel electrode. The processor can be programmed receive an instruction to schedule a sleep program based on a set parameter from another device in wireless communication with the sleep training device. The processor can also be programmed to initiate the sleep program once the parameter is met and disable at least one of the physical switches and the capacitive touch component when the sleep program is initiated. The processor can be programmed to receive a lock instruction from either from a client device or a server via the wireless communication unit and disable the capacitive touch component in response to the lock instruction initiated by the client device.

The sleep training device can include a microphone electrically coupled to the processor configured to detect cries or other sounds in a vicinity of the sleep training device. The sleep training device can also include one or more rechargeable batteries configured to supply power to at least one of the processor, the real-time clock IC, the memory, the wireless communication unit, the audio component, the LEDs, and the physical switches. The wireless communication unit can be a Bluetooth® communication unit including a Bluetooth® processor and a Bluetooth® memory. The wireless communication unit can also be a wireless fidelity (WiFi) communication unit. The sleep training device can also include a Bluetooth® audio interface configured to receive sounds from a client device and communicate such sounds through the speaker of the sleep training device. The sleep training device can also include a gesture control sensor configured to detect a hand gesture made by a user in a vicinity of the gesture control sensor.

A method of remotely locking a sleep training device is also disclosed. The method can comprise receiving an instruction to schedule a sleep program based on a set parameter from another device in wireless communication with the sleep training device. The sleep training device further can comprise a printed circuit board (PCB), comprising a processor, a real-time clock integrated circuit (IC), a memory, and a wireless communication unit, an audio component electrically coupled to the processor, light-emitting diodes (LEDs) electrically coupled to the processor, a number of physical switches electrically coupled to the processor, wherein the physical switches are configured to control at least one of the LEDs and the audio component, a capacitive touch component, and a device housing configured to house the PCB, the audio component, the LEDs, and at least part of the physical switches.

The method can further comprise initiating, using the processor, the sleep program once the set parameter is met and disabling at least one of the physical switches and the capacitive touch component when the sleep program is initiated.

The method can also comprise receiving a lock instruction from at least one of a client device and a server via the wireless communication unit and disabling the at least one of the physical switches and the capacitive touch component in response to the lock instruction received.

BRIEF DESCRIPTION OF THE DRAWINGS

FIGS. 7A and 7B illustrate example GUIs of an application running on a client device configured to control the sleep training device.

FIGS. 10A-10D illustrate other example GUIs of an application running on a client device configured to control the sleep training device.

DETAILED DESCRIPTION

Figure 1A:
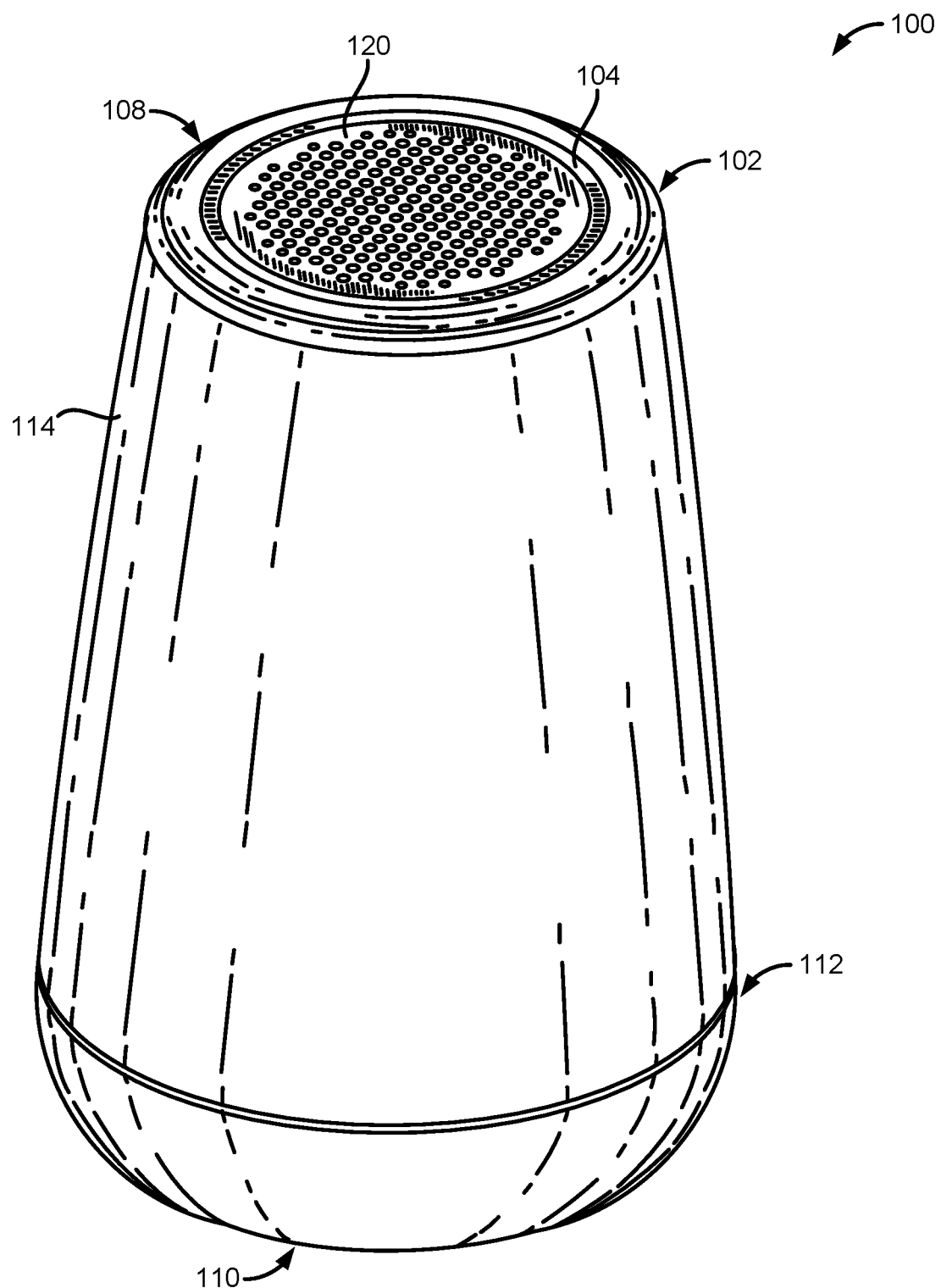
FIG. 1A illustrates a perspective view of an example of a sleep training device having a remote locking mechanism.
Figure 1B:
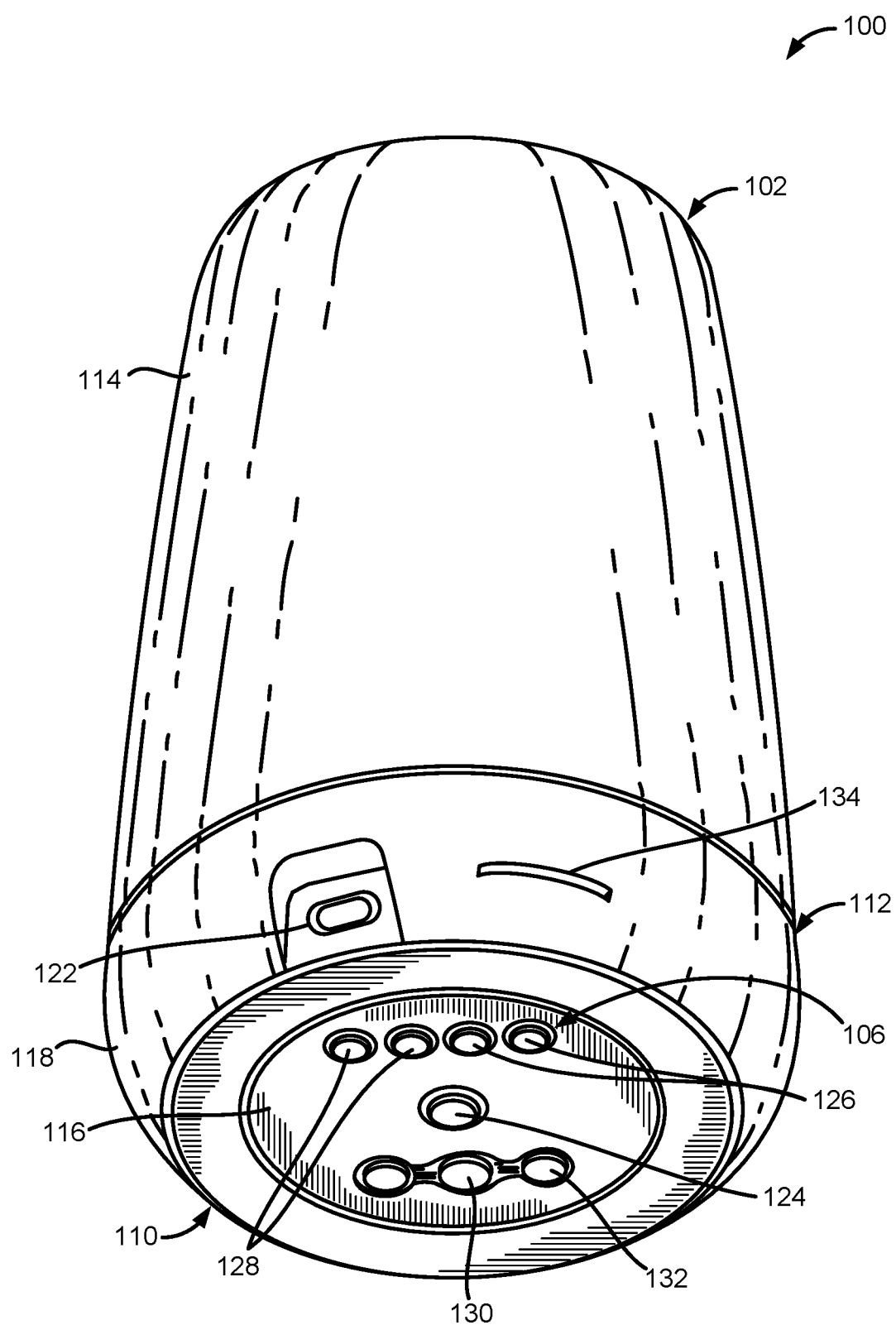
FIG. 1B illustrates a bottom perspective view of the sleep training device.

FIGS. 1A and 1B illustrate that the sleep training device 100 can have a device housing 102, a capacitive touch component 104, and one or more physical switches 106 configured to control certain functions of the device 100. The capacitive touch component 104 can be positioned along a top 108 of the device 100 and the one or more physical switches 106 can be positioned on a bottom 110 of the device 100. In other examples, the capacitive touch component 104 can be positioned along a side of the device housing 102 or closer to the bottom 110 of the device 100. The capacitive touch component 104 can be made in part from stainless steel. The capacitive touch component 104 will be discussed in more detail in the following sections.

As shown in FIGS. 1A and 1B, the device housing 102 can be shaped substantially as a frustoconic having a rounded bottom. The device housing 102 can also be shaped substantially as a conic, a cylinder, a tetrahedron, a square pyramid, a pentagonal pyramid, a hexagonal pyramid, a triangular prism, a cube or cuboid, a hexagonal prism, a trapezoidal prism, a dome, a parallelepiped, a dodecahedron, or a combination thereof. The device housing 102 can be defined by a larger or wider device bottom 110 and smaller or converging device top 108 to enhance the stability of the device 100 when the device 100 is placed on a substantially flat surface such as a tabletop, countertop, shelf, or nightstand top.

The device housing 102 can comprise a housing base 112 and a light diffusing cover 114. The housing base 112 can be substantially acetabular or shaped as a bowl or a cup surrounded by a parabolic perimeter wall. The housing base 112 can also be shaped substantially as a frustoconic, a cylinder, a cube or cuboid, a hexagonal prism, a trapezoidal or polygonal prism, a dome, a parallelepiped, or a combination thereof.

As shown in FIG. 1B, the housing base 112 can comprise a base plate 116 and a base enclosure 118. The base plate 116 can be substantially circular, triangular, rectangular, or another type of polygon-shape, rectangular with rounded corners, oval, rhombus-shaped, or a combination thereof. The base plate 116 can have one or more cutouts, bores, or openings defined along the surface of the base plate 116 to accommodate the one or more physical switches 106.

The base plate 116 can also comprise or be covered by a friction pad or friction inducing surface or surface feature to prevent the device 100 from sliding off a placement surface or being inadvertently moved by a user when the user contacts the capacitive touch component 104. The friction pad can be made of or comprise rubber, synthetic rubber, a polymer having a high friction coefficient, or a combination thereof. The base plate 116 can also be defined by or have a friction inducing pattern such as a waffled pattern, a pock-marked pattern, a grooved pattern, a lined indentation pattern, or a combination thereof.

The light diffusing cover 114 can be coupled to the housing base 112. In one variation, the light diffusing cover 114 can be detachable or separable from the housing base 112. In other variations, the light diffusing cover 114 can be affixed to the housing base 112 by adhesives, fasteners, a threaded connection, or a combination thereof.

FIG. 1A illustrates that the device housing 102 can also comprise a covering plate 120 at the top 108 of the device 100. The covering plate 120 can be a speaker grill or cover when the covering plate 120 is positioned above or in a vicinity of a speaker 204 within the device housing 102. As shown in FIG. 1A, the covering plate 120 can be substantially circular having multiple openings, holes, cutouts, slots, slits, or a combination thereof defined on the covering plate 120. The covering plate 120 can also be substantially triangular, rectangular or another type of polygon-shape, rectangular with rounded corners, oval, rhombus-shaped, or a combination thereof.

When the covering plate 120 is substantially circular-shaped, the capacitive touch component 104 can be shaped substantially as an annulus or ring surrounding or circumscribing the covering plate 120. The shape or design of the capacitive touch component 104 can match the shape or design of the covering plate 120 such that the capacitive touch component 104 surrounds or encloses the covering plate 120. In other variations, the capacitive touch component 104 can include at least part of the covering plate 120. For example, both the annular ring surrounding the covering plate 120 and the covering plate 120 can serve as the capacitive touch component 104 and both can be made in part from stainless steel. The capacitive touch component 104 can also be accessible through an opening or cutout defined within the covering plate 120.

FIG. 1B illustrates that the device 100 can also comprise a power supply port 122. The power supply port 122 can be accessed through openings or cutouts defined along the housing base 112. The power supply port 122 can also be accessed through openings or cutouts defined along the light diffusing cover 114. The power supply port 122 can include a universal serial bus (USB) port such as a micro USB, a mini USB port, or a USB-C port. The power supply port 122 can also be a coaxial barrel receptacle for receiving a coaxial barrel connector. For example, the power supply port 122 can receive a connector of a universal alternating current (AC) adapter. The device 100 can also have no power supply ports 122 and can have an inductive charge receiver housed within the device housing 102 for receiving wireless power.

As shown in FIG. 1B, the device 100 can also include one or more physical switches 106 including an on/off switch 124, volume control switches 126, brightness control switches 128, sound control switches including a play button 130 and one or more track selection buttons 132, a memory card slot 134, or a combination thereof. The one or more physical switches 106 can be implemented as push-button switches, toggle switches, or a combination thereof. In some variations, the one or more physical switches 106 can also comprise one or more capacitive touch components or sensors.

The on/off switch 124 can allow a user to power on or activate the device 100 by physically pressing or actuating the on/off switch 124. The volume control switches 126 can allow a user to control the volume level of sounds generated by one or more speakers 204 (see FIG. 2) housed within the device housing 102. The brightness control switches 128 can allow a user to control the brightness or luminous intensity of light generated by LEDs 206 (see FIG. 2) housed within the device housing 102. The play button 130 can allow a user to initiate, resume, or pause a preset sound or tune such as a white-noise sound, one or more lullabies, one or more environmental sounds, or any other machine generated sounds. The track selection buttons 132 can also allow a user to cycle through a number of preset sound options or tunes.

The device housing 102 including the housing base 112, the light diffusing cover 114, or a portion thereof can be made of or comprise a polymeric material, a metallic material, or a combination thereof. In some variations, a portion of the device housing 102 can be made of an organic material such as wood or bamboo.

For example, the device housing 102 including the housing base 112, the light diffusing cover 114, or any portion thereof can be made of or comprise a thermoplastic. The device housing 102 including the housing base 112, the light diffusing cover 114, or any portion thereof can be made of or comprise acrylonitrile butadiene styrene (ABS), polycarbonate (PC), polypropylene (PP), one or more acrylics including opal acrylic, or a combination thereof. For example, the housing base 112 can be manufactured as one molded piece of ABS plastic.

The light diffusing cover 114 can be made of or comprise a polymeric material configured to diffuse or soften light generated by the LEDs 206 within the device housing 102. The light diffusing cover 114 can also be made of or comprise a polymeric material configured to dissipate heat generated by the LEDs 206. For example, the light diffusing cover 114 can be made of or comprise ABS, polycarbonate, or a combination thereof. The light diffusing cover 114 can also comprise or be defined by one or more surface features or textures configured to diffuse light generated by the LEDs 206. The light diffusing cover 114 can also be covered by one or more coatings configured to diffuse light or dissipate heat generated by the LEDs 206.

Figure 1C:
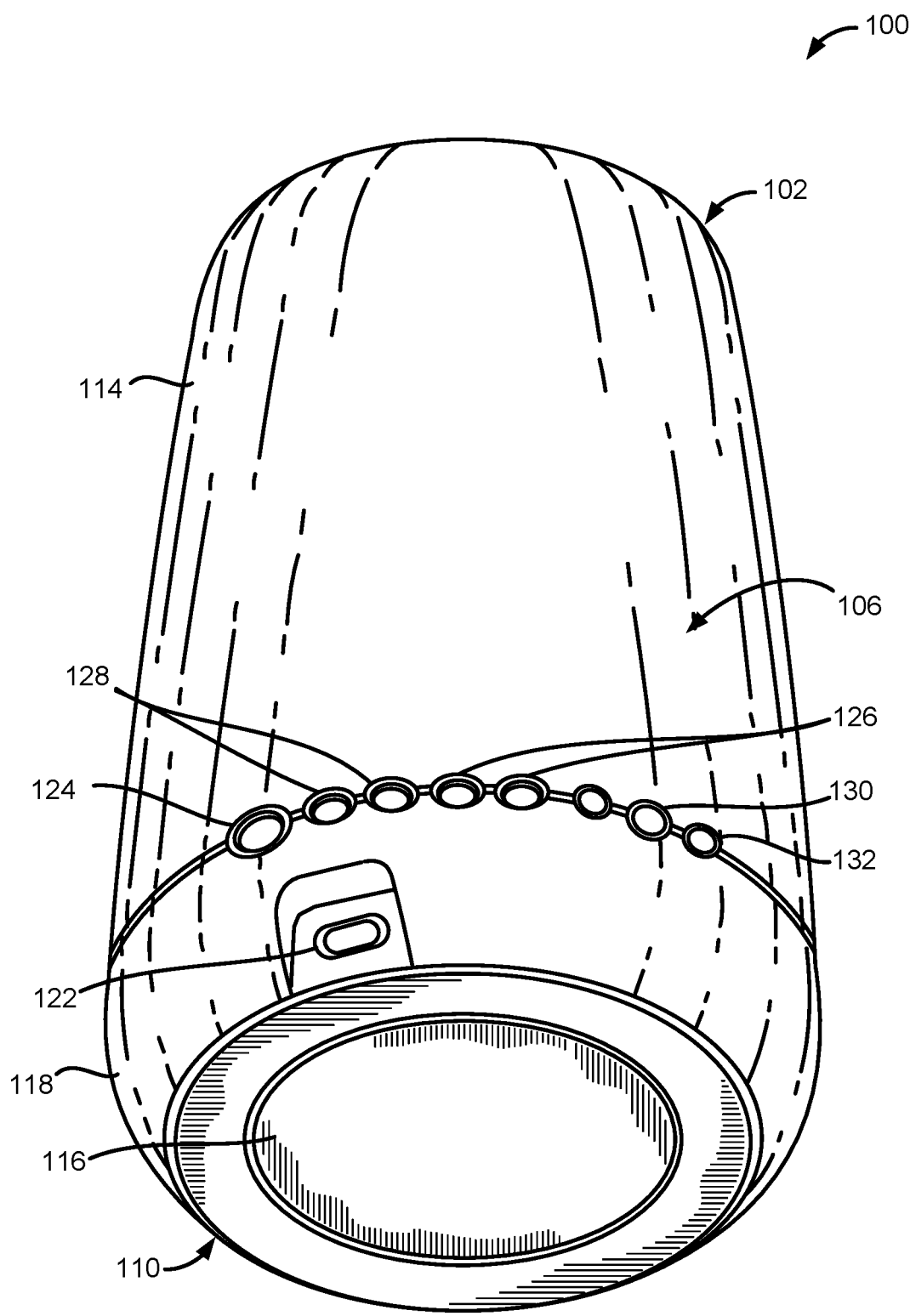
FIG. 1C illustrates another bottom perspective view of the sleep training device.

FIG. 1C illustrates that the one or more physical switches 106, such as any of the on/off switch 124, the volume control switches 126, the brightness control switches 128, the play button 130, and the one or more track selection buttons 132, can be positioned on a side of the device 100. More specifically, the one or more physical switches 106 can be positioned between the light diffusing cover 114 and the base enclosure 118.

Figure 2:
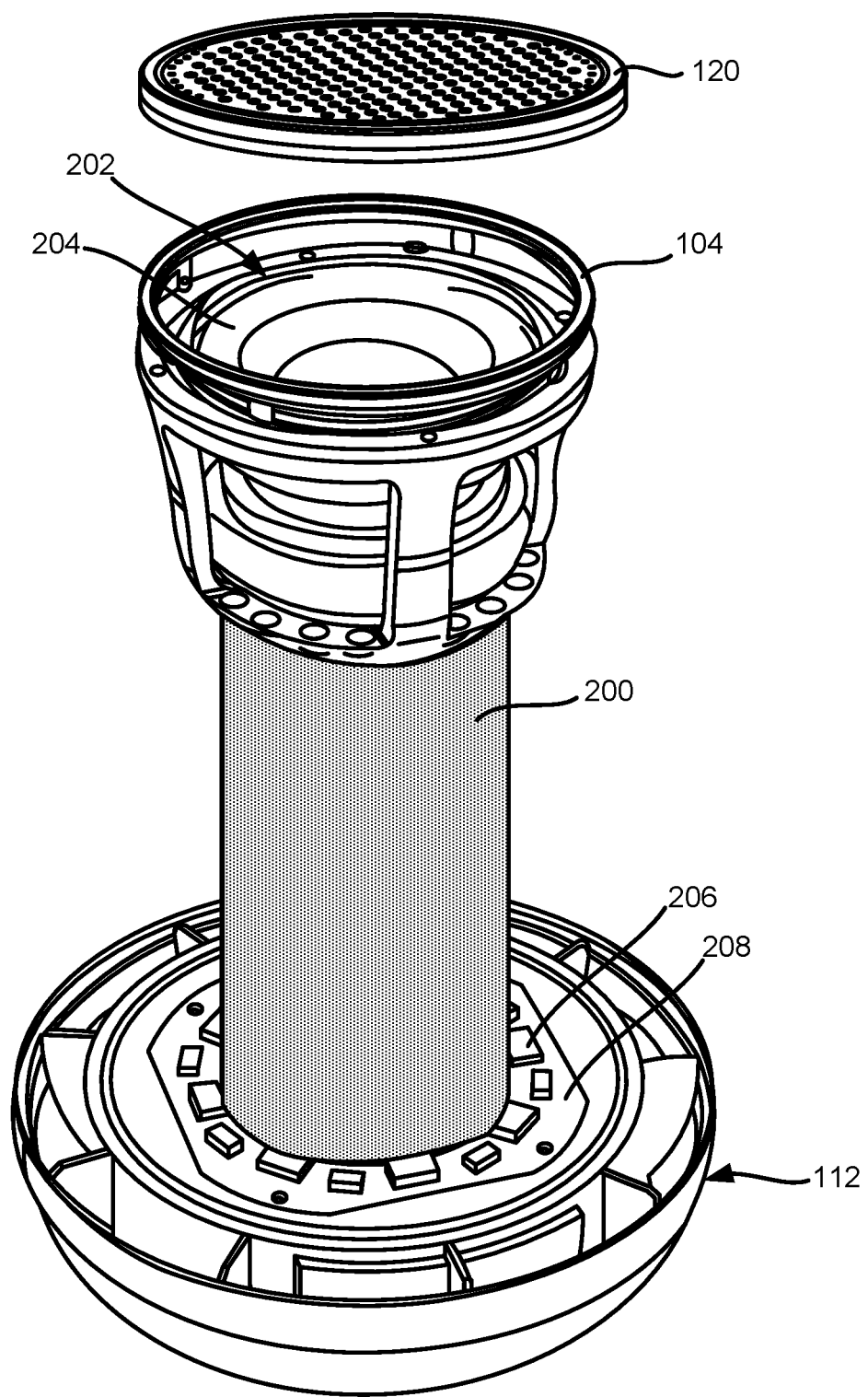
FIG. 2 illustrates the sleep training device with a light diffusing cover removed and a covering plate separated from the speaker.

FIG. 2 illustrates that the device 100 can have a support column 200 extending vertically upward from the housing base 112. As shown in FIG. 2, the support column 200 can be substantially shaped or designed as a cylinder. The support column 200 can also be substantially shaped as a conic, a frustoconic, a cuboid, a prism, a pyramid, or a combination thereof. The support column 200 can be configured to hold up a part of an audio component 202 of the device 100 including a speaker 204 controlled by one or more electronic components of the device 100.

As shown in FIG. 2, the housing base 112 can at least partially house or enclose a number of the LEDs 206. The LEDs 206 can be affixed or otherwise electrically coupled to an LED board 208. As shown in FIG. 2, the LEDs 206 can be arranged in a circular pattern surrounding the support column 200. For example, the LEDs 206 can be arranged in a ring-like pattern around a perimeter of the support column 200. The LEDs 206 can also be arranged in a rectangular pattern, a rhombus-shaped pattern, a triangular pattern, or an oval pattern around the support column 200. The LEDs 206 can also only partially surround, border, or circumscribe the support column 200. Although only a single file and one level arrangement of LEDs 206 is shown in FIG. 2, it is contemplated by this disclosure that multiple layers or levels of LEDs 206 can be stacked on top of one another or arranged in a helical pattern around the support column 200. In other variations, multiple rings of LEDs 206 can encircle or surround the support column 200. The LEDs 206 can also be arranged such that each LED 206 is separated from its adjacent neighboring LED 206 by a space or gap.

As shown in FIG. 2, the LEDs 206 can be positioned near the bottom of the support column 200 and positioned within the housing base 112. The LEDs 206 can also be positioned near a vertical middle of the support column 200 such that the LED board 208 is raised above the housing base 112. In these and other variations, the LEDs 206 can also be positioned near a top of the support column 200 closer to the speaker 204.

The LEDs 206 can include one or more red-green-blue-white (RGBW) LEDs. The LEDs 206 can also include one or more active-matrix organic light-emitting diodes (AMOLED), a super AMOLEDs, or a combination thereof.

In addition to supporting the speaker 204 or any other parts of the audio component 202, the support column 200 can also house or act as a container for one or more electrical components such as wires, circuits, conductors, interfaces, circuit boards, power supply components, or a combination thereof connecting a processor or another circuit or chip on the PCB 300 (see FIG. 3A-3B or FIG. 5) to the speaker 204, another part of the audio component 202, the capacitive touch component 104, or a combination thereof. The support column 200 can also be used to house, contain, or store a portable power supply such as one or more batteries 302 (see FIG. 3A-3B).

The support column 200 can be covered by an opaque material such as an additional polymeric layer or coating to prevent the electrical components or wires enclosed or partially housed within the support column 200 from casting shadows from light generated by the LEDs 206 within the device housing 102. For example, the support column 200 can be covered by an opaque coating, an opaque polymeric layer, a fabric covering or layer, a metallic material, or a combination thereof. The outer side surface or perimeter surface of the support column 200 can also comprise or be defined by one or more surface features such that the electrical components or wires within the support column 200 do not cast shadows from light generated by the LEDs 206 within the device housing 102.

The capacitive touch component 104 can be made of or comprise a metallic material, a semiconductor material, or a combination thereof. For example, the capacitive touch component 104 can be made of or comprise stainless steel. As shown in FIG. 2, the capacitive touch component 104 can be a stainless steel electrode substantially shaped as an annulus or ring. In other variations, at least part of the covering plate 120 can be the capacitive touch component 104.

Figure 3A:
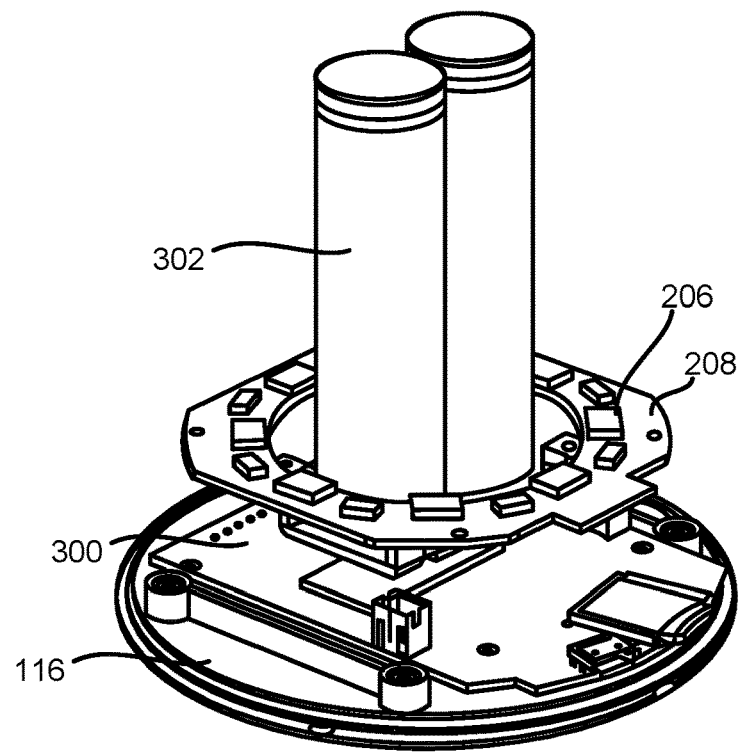
FIG. 3A illustrates an example of certain electronic components housed within the sleep training device.
Figure 3B:
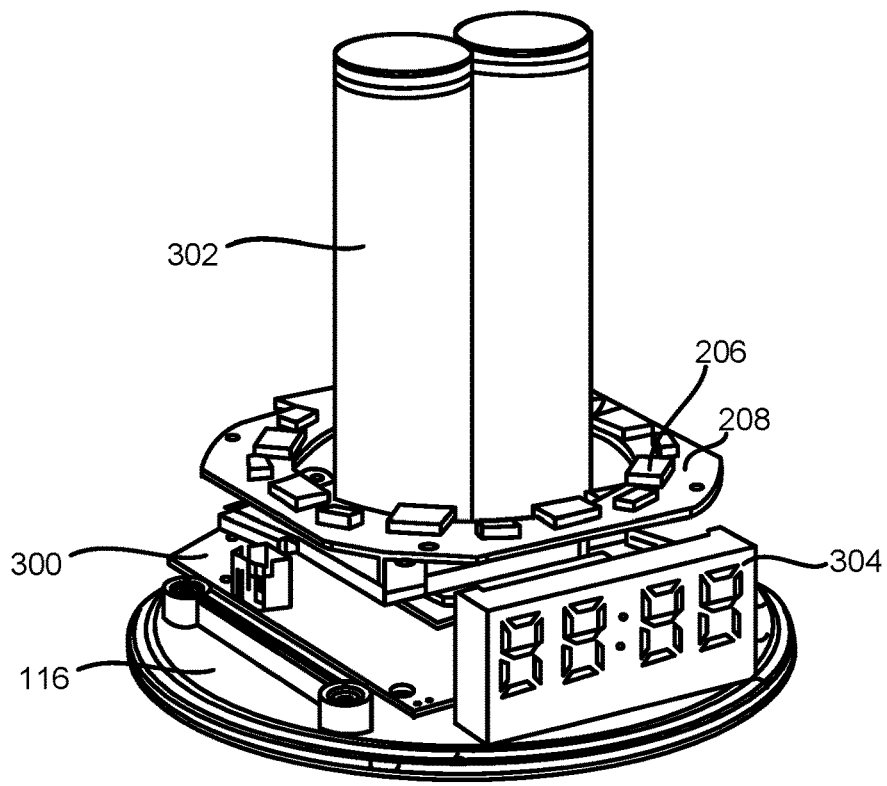
FIG. 3B illustrates an example of certain electronic components housed within the sleep training device.

FIG. 3A illustrates that a printed circuit board (PCB) 300 comprising a number of chips, modules, ICs, sensors, interfaces, and high-speed buses can be housed within the device housing 102. FIGS. 3A and 3B show examples of the PCB 300 coupled to the base plate 116 of the housing base 112 with the support column 200 and the base enclosure 118 removed. FIGS. 3A and 3B also illustrate that the LED board 208 can be coupled to the PCB 300 and housed within the device housing 102. The LED board 208 can be positioned above the PCB 300 or elevated from the PCB 300 such that the LED board 208 and the LEDs 206 are separated from the electrical components on the PCB 300 by a gap or distance.

The PCB 300 and the LED board 208 can be coupled to one another or to the interior of the device housing 102 by fasteners, screws, thread connections, interference fit, clips, clasps, adhesives, heat staking, thermoplastic staking via laser welding or ultrasonic welding, or a combination thereof. For example, the PCB 300, the LED board 208, or a combination thereof can be coupled to polymeric studs, posts, ribs, bosses, or any combination thereof protruding from an interior surface of a part of the device housing 102 through holes or slots on any of the boards via staking or an interference fit.

FIG. 3B illustrates that the device 100 can also comprise a clock display 304. The clock display 304 can comprise a LED clock display, a liquid crystal display (LCD), or a combination thereof. The clock display 304 can project the time through the base enclosure 118 or the light diffusing cover 114 depending on the position of the clock display 304 within the device housing 102.

FIGS. 3A and 3B also illustrate that the cavity, void, or hollow within the LED board 208 can also accommodate one or more batteries 302. The batteries 302 can be housed within the support column 200 (see FIG. 2). The batteries 302 can be backup batteries to back up the power supplied through the power supply port 122 or the batteries 302 can power the entire device 100. The device housing 102 can also have additional receptacles or cavities for housing or accommodating the batteries 302 separate from the support column 200.

The batteries 302 can include rechargeable batteries, one-time use batteries, or a combination thereof. For example, the batteries 302 can include multiple C size batteries or multiple AA size batteries. The batteries 302 can be alkaline batteries, lithium ion batteries, nickel cadmium batteries, or nickel metal hydride batteries. Although not shown in FIGS. 3A and 3B, the interior of the support column 200 can also house or surround one or more wires, conduits, ducts, conductors, circuits, or other electrical components running from the PCB 300 to the speaker 204, another part of the audio component 202, the capacitive touch component 104, or a combination thereof.

Figure 3C:
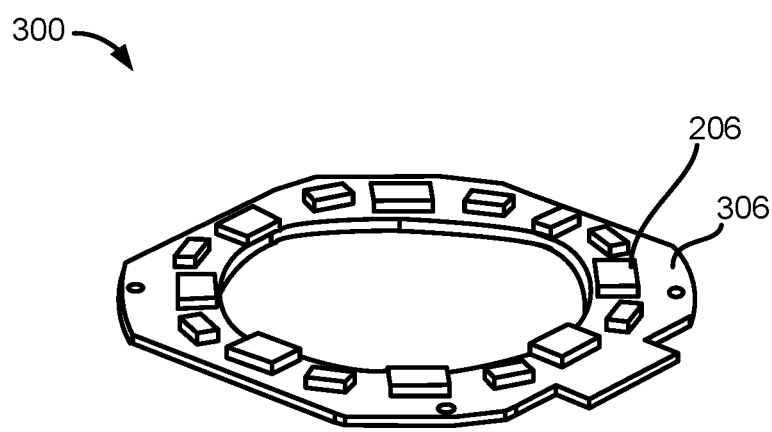
FIGS. 3C and 3D illustrate a variation of a printed circuit board (PCB) of the sleep training device that incorporates LEDs on one side of the PCB and electronic components on a reverse side of the PCB, respectively.
Figure 3D:
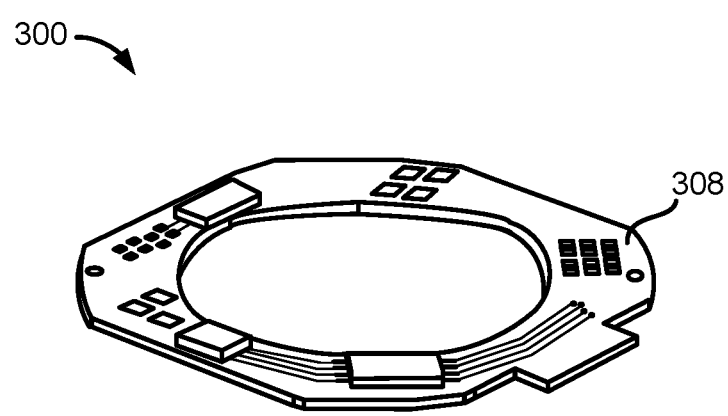

FIGS. 3C and 3D illustrate a variation of the PCB 300 that incorporates the LEDs 206 on one side 306 of the PCB 300 (see FIG. 3C) and certain electronic components of the device 100 (for example, any of the components shown in FIG. 5) on a reverse side 308 of the PCB 300 (see FIG. 3D).

Figure 4A:
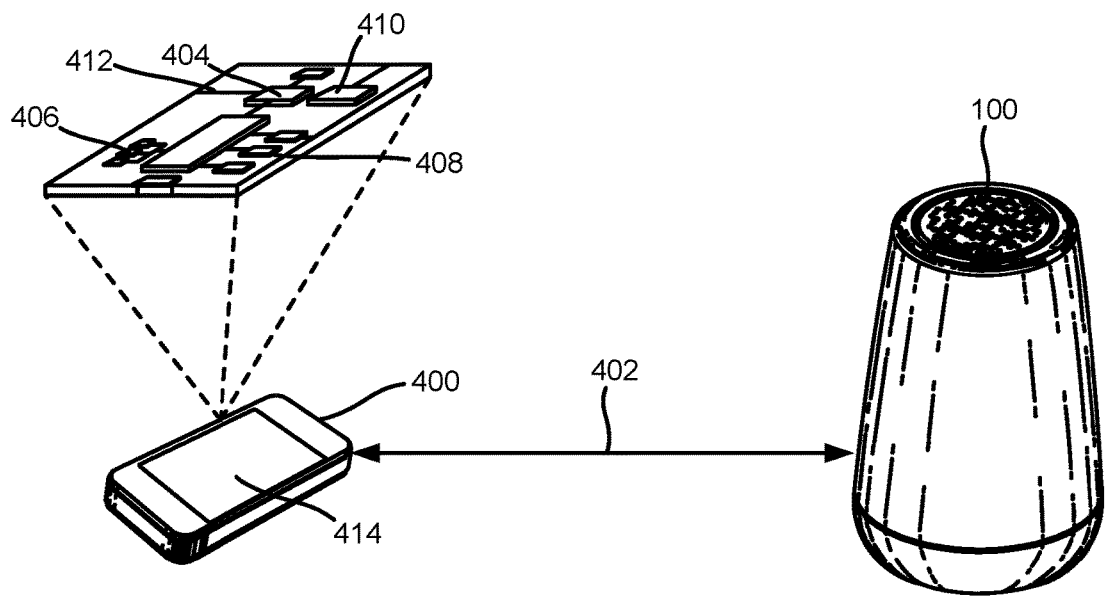
FIG. 4A illustrates an example sleep training system including a client device which can be configured to remotely control the sleep training device.

FIG. 4A illustrates that a client device 400 can be in wireless communication directly with the device 100 through a short-range wireless communication protocol 402. The short-range wireless communication protocol 402 can be a Bluetooth® protocol 402 (such as a Bluetooth® Low Energy (BLE) protocol). The short-range wireless communication protocol 402 can also be a ZigBee® protocol, a near-field communication (NFC) protocol, or any combination thereof.

The client device 400 can be a portable computing device such as a smartphone, a tablet, a laptop, a smartwatch, a personal entertainment device, or a combination thereof. In other variations not shown in FIG. 4A, the client device 400 can be a desktop computer, a workstation, another server, or a combination thereof. The client device 400 can have a client processor 404, a client memory 406, a communication unit 408, and a locational unit 410 having a global navigation satellite system (GNSS) receiver, such as a global positioning system (GPS) receiver. The client processor 404 can be coupled to the client memory 406, the communication unit 408, and the locational unit 410 through high-speed buses 412.

The client processor 404 can include one or more CPUs, GPUs, ASICs, FPGAs, or a combination thereof. The client processor 404 can execute software stored in the client memory 406 to execute the methods described herein. The client processor 404 can be implemented in a number of different manners. For example, the client processor 404 can be an embedded processor, a processor core, a microprocessor, a logic circuit, a hardware FSM, a DSP, or a combination thereof. As a more specific example, the client processor 404 can be a 32-bit processor such as an ARM™ processor.

The client memory 406 can store software, data, logs, or a combination thereof. In one variation, the client memory 406 can be an internal memory. In another variation, the client memory 406 can be an external storage unit. The client memory 406 can be a volatile memory or a non-volatile memory. For example, the client memory 406 can be a nonvolatile storage such as NVRAM, Flash memory, disk storage, or a volatile storage such as SRAM. The client memory 406 can be the main storage unit for the client device 400.

The communication unit 408 can be a wired or wireless communication interface. For example, the communication unit 408 can be a network interface card of the client device 400. The communication unit 408 can be a wireless modem or a wired modem. In one variation, the communication unit 408 can be a WiFi modem. In other variations, the communication unit 408 can be a 3G modem, a 4G modem, an LTE modem, a Bluetooth® component, a radio receiver, an antenna, or a combination thereof. The client device 400 can connect to or communicatively couple with a WLAN, a wide area network, or a combination thereof using the communication unit 408. The client device 400 can transmit or receive packets or messages using the communication unit 408.

The locational unit 410 can have a GPS component such as the GPS receiver, an inertial unit, a magnetometer, a compass, or any combination thereof. The locational unit 410 can receive GPS signals from a GPS satellite. The inertial unit can be implemented as a multi-axis accelerometer including a three-axis accelerometer, a multi-axis gyroscope including a three-axis MEMS gyroscope, or a combination thereof.

The client device 400 can also have a display 414. The display 414 can be a liquid crystal display (LCD) touchscreen, a lighting-emitting diode (LED) touchscreen, an active-matrix organic light-emitting diode (AMOLED) touchscreen, a super AMOLED touchscreen, or a combination thereof.

In certain variations, the display 414 can be a retina display, a haptic touchscreen, or a combination thereof. For example, when the client device 400 is a smartphone, the display 414 can be the touchscreen display of the smartphone.

Although not shown in the figures, it is contemplated by this disclosure that the client device 400 can be a standalone console or hub having a console processor, a console memory, a console communication unit, and a console display. The console or hub can be a dedicated wireless communication device for wirelessly connecting the device 100 with the client device 400.

Figure 4B:
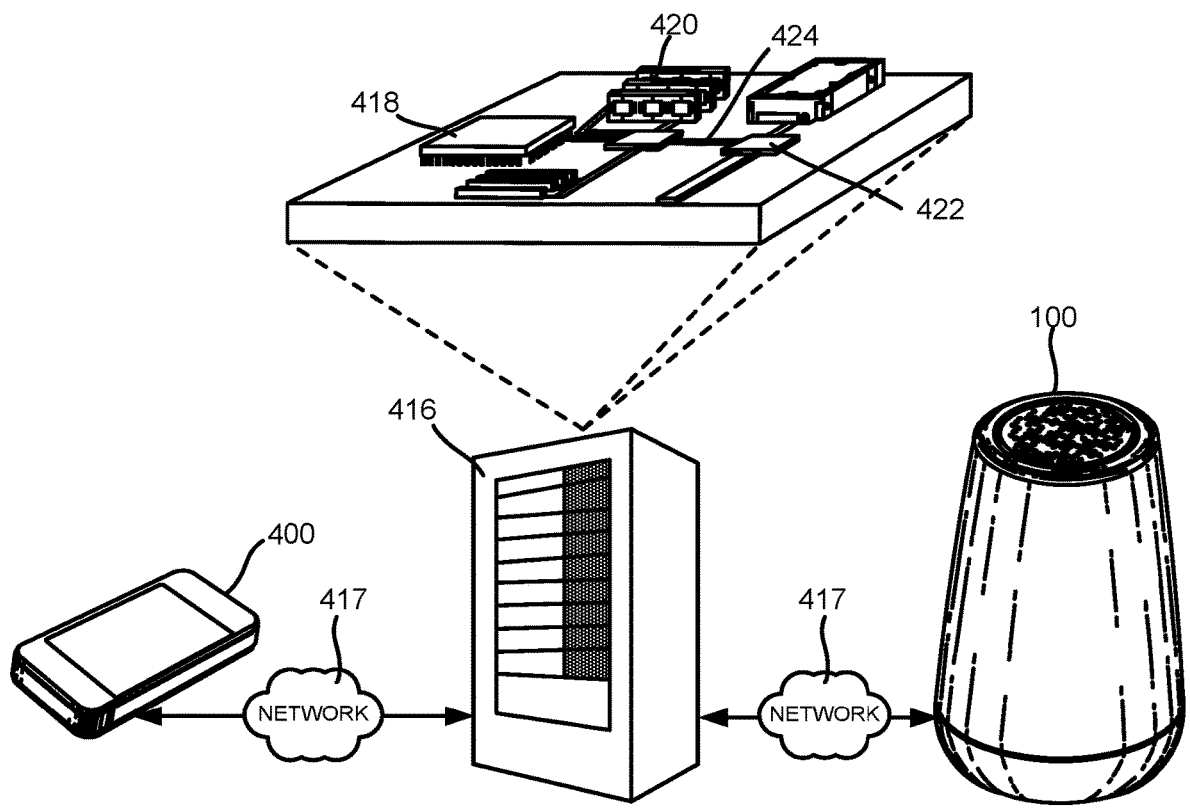
FIG. 4B illustrates another example of a sleep training system including a client device and a server which can be configured to remotely control the sleep training device.

FIG. 4B illustrates that the client device 400 can also be in wireless communication with the device 100 through a server 416 and one or more networks 417. The networks 417 can include any multi-hop network or wide area network (WAN) that covers regions, countries, continents, or a combination thereof. Examples of the networks 417 can include a cellular network such as a 3G network, a 4G network or a long-term evolution (LTE) network, a satellite network; a sonic communication network; the Internet; or a combination thereof. The networks 417 can include a number of wireless local area networks (WLANs). The WLANs can include networks established under the IEEE's 802.11 protocol or a successor thereof. For example, the WLANs can include a number of wireless-fidelity (WiFi) networks.

The server 416 can have a processing unit 418, a memory unit 420, and a server communication unit 422. The processing unit 418 can be coupled to the memory unit 420 and the server communication unit 422 through high-speed buses 424.

Figure 4C:
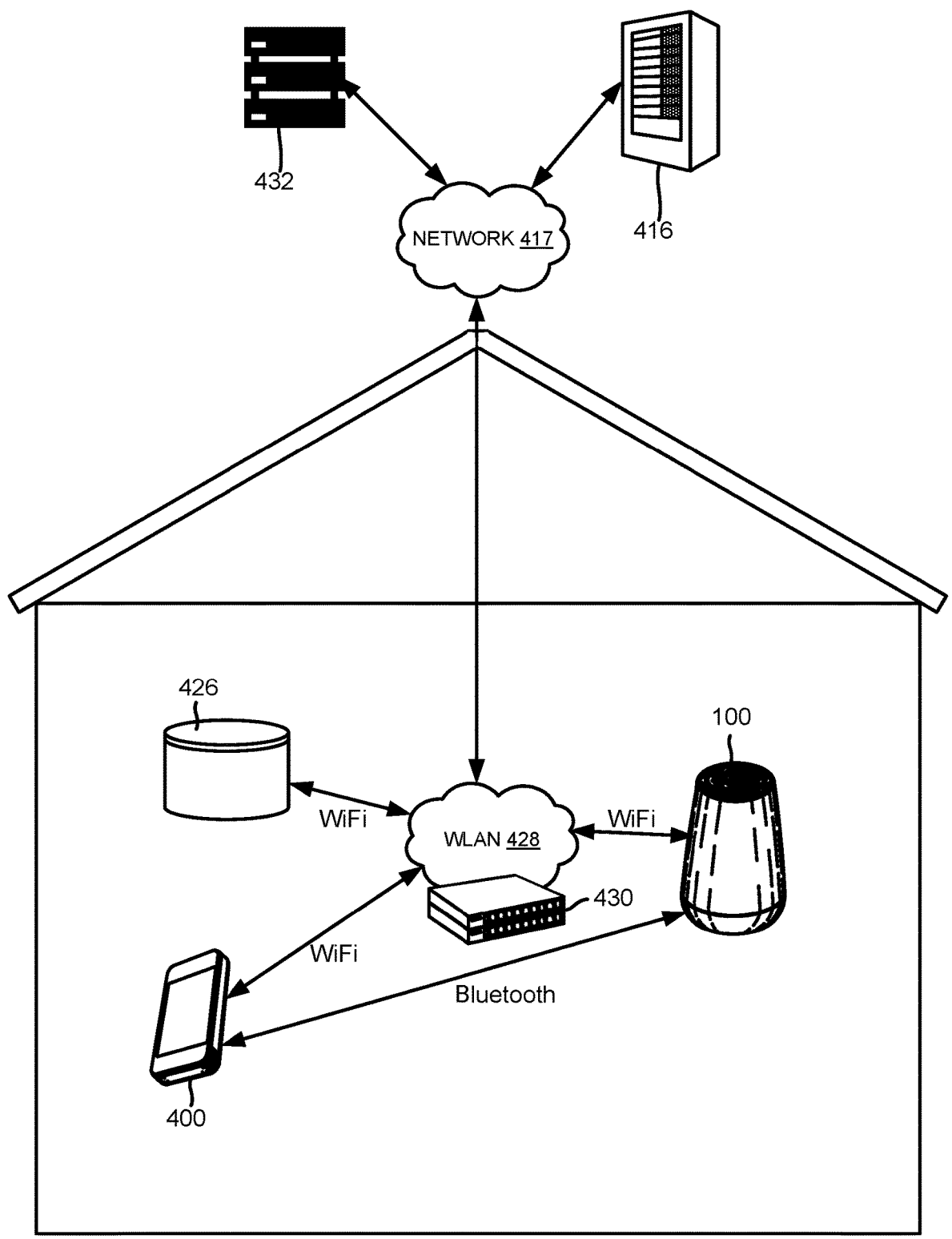
FIG. 4C illustrates another example of a sleep training system including the sleep training device, a client device, and a voice-enabled assistance device.

FIG. 4C illustrates that another variation of the sleep training system can include the sleep training device 100, a client device 400, and a voice-enabled assistance device 426. The voice-enabled assistance device 426 can include an Amazon Echo™ device, an Amazon Echo Dot™, an Amazon Echo Spot™ device, an Amazon Echo Show™ device, a Google Home™ device, a Google Home Mini™ device, a Google Home Max™ device, or another smart home controller or hub device.

As shown in FIG. 4C, the sleep training device 100, the client device 400, and the voice-enabled assistance device 426 can be communicatively coupled to a wireless local area network (WLAN) 428 set up by a wireless gateway or wireless router 430. The sleep training device 100, the client device 400, and the voice-enabled assistance device 426 can connect to another network 417 (e.g., a WAN such as the Internet) via the wireless gateway or wireless router 430. As previously mentioned, the client device 400 can also connect directly to the sleep training device 100 via a short-range wireless communication protocol 402 (e.g., Bluetooth® or BLE).

The voice-enabled assistance device 426 can communicate with a voice-enabled assistance server 432 via the network 417. The voice-enabled assistance device 426 can detect a voice command from a user to have the sleep training device 100 undertake an action. For example, the action can include activating or deactivating the sleep training device 100 (i.e., turning the sleep training device 100 ON or OFF); adjusting a volume level of sounds generated by the one or more speakers 204 of the sleep training device 100; playing, pausing, or resuming a track or sound stored in the system memory 501 of the sleep training device 100 or streamed by the sleep training device 100; initiating or stopping a timer function of the sleeping training device 1000, adjusting a brightness or luminous intensity of light generated by the LEDs 206, adjusting the color(s) of the light generated by the LEDs 206, enabling or initiating a lock function 1300, downloading multimedia content from the server 416 or another device, downloading software updates from the server 416 or another device, or a combination thereof.

The voice-enabled assistance device 426 can parse the voice command and transmit the parsed voice command to the voice-enabled assistance server 432. The voice-enabled assistance server 432 can process the parsed voice command based on stored rules and automation processes stored in one or more databases accessible to the voice-enabled assistance server 432. The voice-enabled assistance server 432 can then transmit a corresponding instruction or command directly to the sleep training device 100 or to the server 416 via one or more application programming interfaces (APIs) and the server 416 can then transmit the instruction or command to the sleep training device 100.

The processing unit 418 can include one or more CPUs, graphical processing units (GPUs), Application-Specific Integrated Circuits (ASICs), field-programmable gate arrays (FPGAs), or a combination thereof. The processing unit 418 can execute software stored in the memory unit 420 to execute the methods described herein. The processing unit 418 can be implemented in a number of different manners. For example, the processing unit 418 can be an embedded processor, a processor core, a microprocessor, a logic circuit, a hardware finite state machine (FSM), a digital signal processor (DSP), or a combination thereof. As a more specific example, the processing unit 418 can be a 64-bit processor.

The memory unit 420 can store software, data, logs, or a combination thereof. The memory unit 420 can be an internal memory. Alternatively, the memory unit 420 can be an external memory, such as a memory residing on a storage node, a cloud server, or a storage server. The memory unit 420 can be a volatile memory or a non-volatile memory. For example, the memory unit 420 can be a nonvolatile storage such as non-volatile random access memory (NVRAM), Flash memory, disk storage, or a volatile storage such as static random access memory (SRAM). The memory unit 420 can be the main storage unit for the server 416.

The server communication unit 422 can include one or more wired or wireless communication interfaces. For example, the server communication unit 422 can be a network interface card of the server 416. The server communication unit 422 can be a wireless modem or a wired modem. In one variation, the server communication unit 422 can be a WiFi modem. In other variations, the server communication unit 422 can be a 3G modem, a 4G modem, an LTE modem, a Bluetooth® component, a Bluetooth® Low Energy (BLE) component, a radio receiver, an antenna, or a combination thereof. The server 416 can connect to or communicatively couple with a WLAN, a wide area network, or a combination thereof using the server communication unit 422. The server 416 can transmit or receive data packets or messages using the server communication unit 422.

Figure 5:
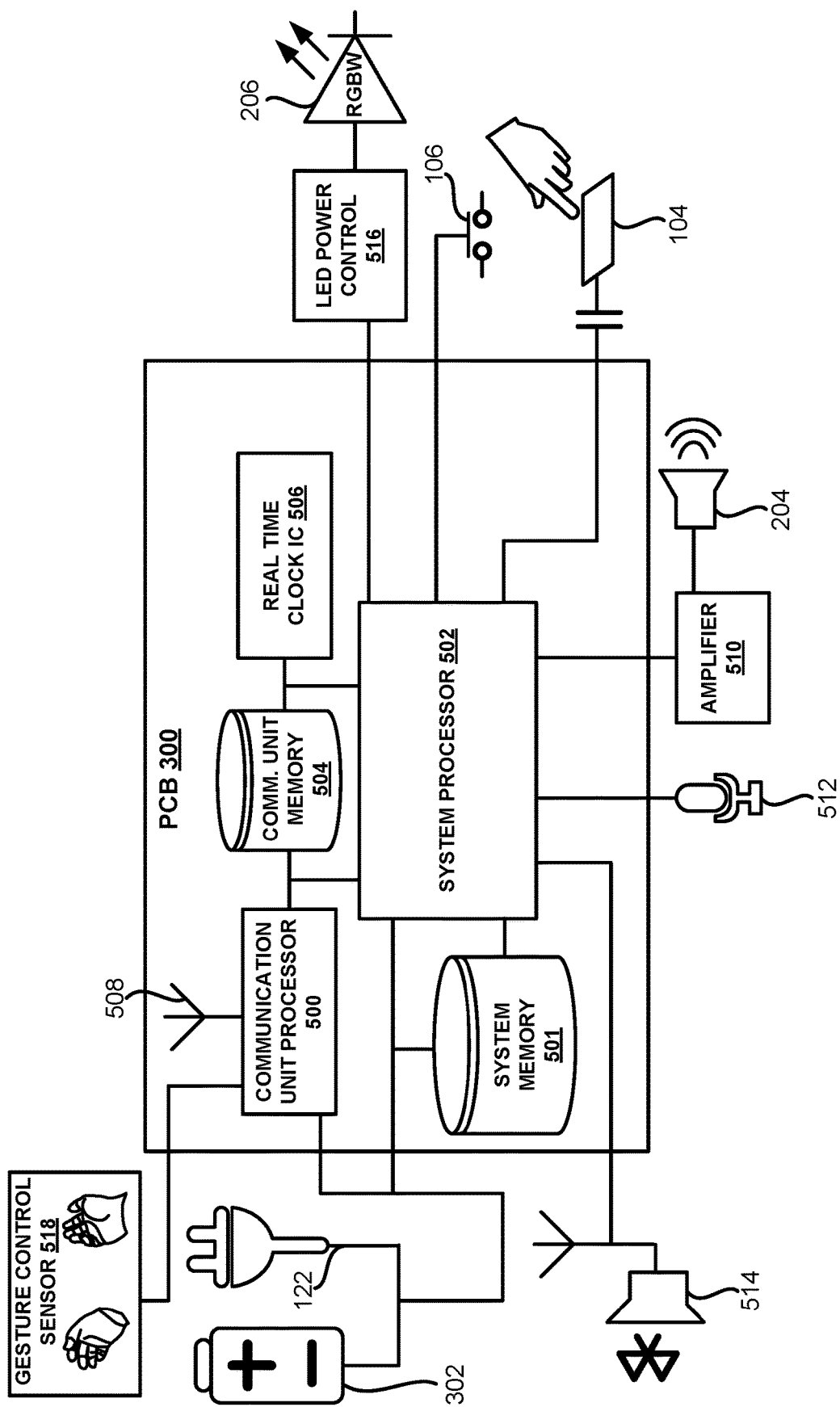
FIG. 5 illustrates a schematic block diagram of certain electronic components of the sleep training device.

FIG. 5 illustrates that the device 100 can be controlled by one or more processors coupled to the PCB 300. The one or more processors can include a communication unit processor 500, a system processor 502, or a combination thereof. The communication unit processor 500 can be part of a communication chip along with a communication unit memory 504 and a real time clock IC 506. The real time clock IC 506 can be used by the processors to keep track of time when a user initiates a timer function through the application 602 on the client device 400 or sets a time-specific sleep program 1002.

The communication chip can be part of a communication module coupled to the PCB 300. The communication unit processor 500 can also be coupled to an antenna 508.

For example, the communication module can be a Bluetooth® module and the communication chip can be a Bluetooth® communication chip and the antenna 508 can be a Bluetooth® antenna. As a more specific example, the Bluetooth® communication chip can be a Nordic® nRF51822 Bluetooth® low energy (BLE) chip and the communication unit processor 500 can be a 32-bit ARM® Cortex®-M0 processor.

In other instances, the communication module can be a WiFi module, the communication chip can be a WiFi chip, and the antenna 508 can be a WiFi antenna. Although not shown in FIG. 5, the device 100 can have both a Bluetooth® module or chip and a WiFi module or chip. References to a processor or processors in this disclosure can include references to the communication unit processor 500, the system processor 502, or a combination thereof.

The system processor 502 can be electrically coupled to a system memory 501 for storing sleep programs 1002 created by a user of the device 100 using the client device 400. The system memory 501 can also store music or sounds to be played by one or more speakers 204 of the device 100. The system memory 501 can be a non-volatile computer storage medium such as an electronically erasable programmable read-only memory (EEPROM). The system memory 501 can also comprise a flash memory and at least 16 MB of storage.

The system processor 502 can also be electrically coupled to one or more amplifiers 510 coupled to the speakers 204. The amplifiers 510 can be used to adjust a volume of the speakers 204.

The system processor 502 can be electrically coupled to a microphone 512 for detecting sounds emanating from a child's room. For example, a user can run the application 602 and listen in on cries or other sounds coming from the child's room.

In some instances, the system processor 502 can also be electrically coupled to a Bluetooth® audio interface 514 to allow a user to transmit sounds or audio wirelessly from the client device 400 to be broadcast by the speakers 204 of the device 100.

The system processor 502 can also be coupled to the LEDs 206 via a LED power control 516. The LED power control 516 can be electrically coupled to the LED board 208 or to part of the PCB 300.

FIG. 5 also illustrates that the communication unit processor 500 can be electrically coupled to a gesture control sensor 518. The gesture control sensor 518 can detect gestures initiated by a user of the device 100 in a vicinity of the gesture control sensor 518. A user can control the device 100 using gestures via the gesture control sensor 518 rather than having to manually press the one or more physical switches 106.

Figure 6:
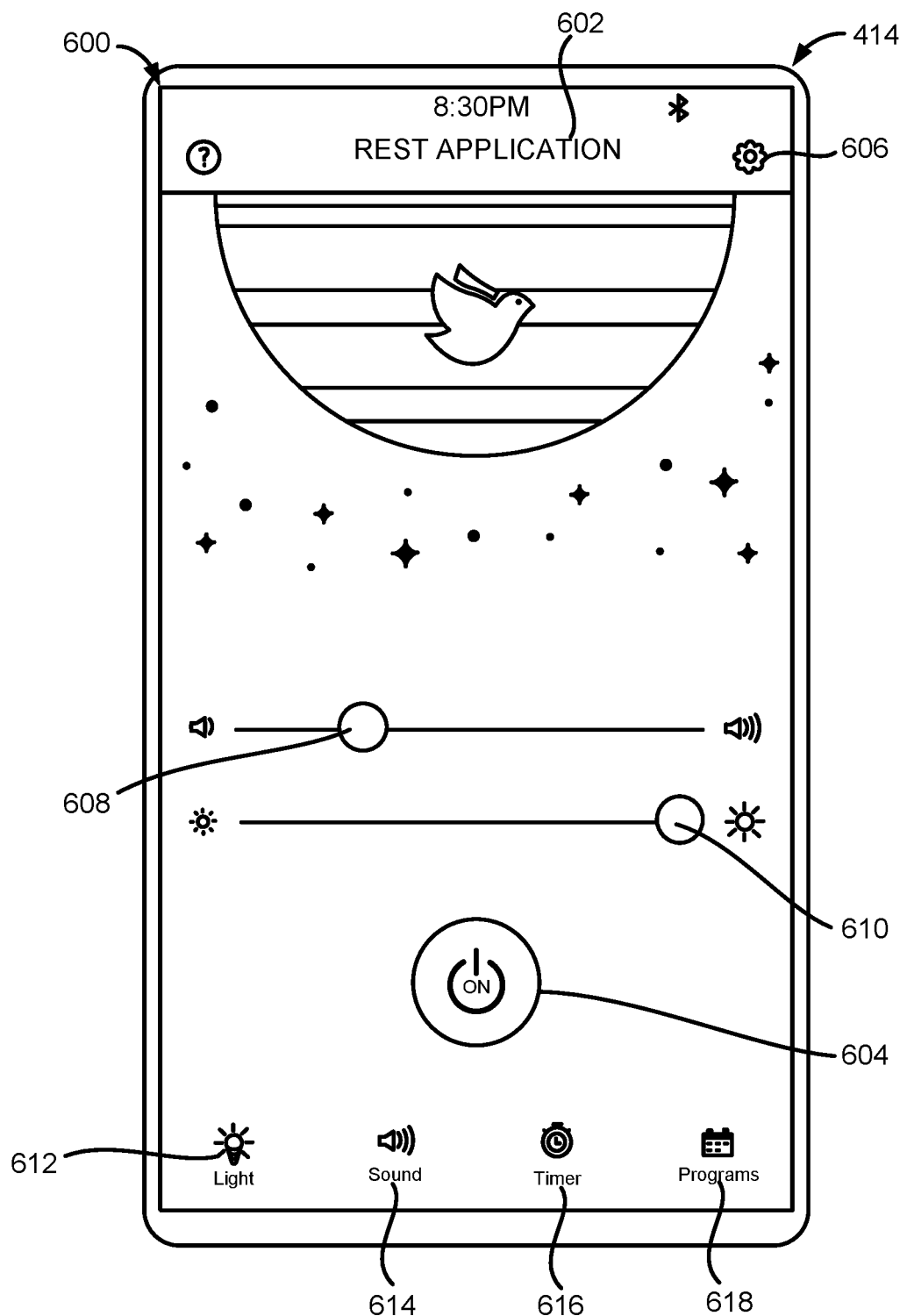
FIG. 6 illustrates an example graphical user interface (GUI) of an application running on a client device configured to control the sleep training device.

FIG. 6 illustrates that a main menu GUI 600 can be rendered by the client device 400 to wirelessly and remotely control the device 100. The main menu GUI 600 can be rendered through an application 602. The application 602 can be written or coded using the Objective-C programming language, the Swift™ programming language, or a combination thereof. The application 602 can also be written using the Java™ programming language, the Python™ programming language, the Objective-C programming language, or a C programming language.

The main menu GUI 600 can be shown on a display 414 of the client device 400 when a user opens up or runs the application 602 on the client device 400. As shown in FIG. 6, the main menu GUI 600 can include an on/off button 604, a settings icon 606, a volume control slider 608, a brightness control slider 610, a light color selection icon 612, a sound selection icon 614, a timer icon 616, and a program icon 618.

The settings icon 606, the light color selection icon 612, the sound selection icon 614, the timer icon 616, and the program icon 618 will be discussed in more detail in further sections. The on/off button 604 can be used to power on or activate the device 100. A user can apply a user input to the on/off button 604 to power on or activate the device 100. The on/off button 604 can be displayed through one or more GUIs of the application 602 whenever the device 100 is powered off or deactivated. As shown in FIG. 1B, the device 100 can also be powered on or activated when a user manually presses the on/off switch 124 or when the user touches the capacitive touch component 104.

The volume control slider 608 can be used to remotely control a volume level of sounds generated by the audio component 202. The processor can instruct the amplifier 510 to adjust the volume level of sounds produced by the speaker 204 in response to a user input applied to the volume control slider 608. As shown in FIG. 1B, the volume level of sounds generated by the audio component 202 can also be controlled by a user manually pressing one or more volume control switches 126 on the device 100.

The brightness control slider 610 can be used to remotely control a brightness or luminous intensity of the light generated by the LEDs 206. The processor can instruct the LED power control 516 to adjust the brightness or luminous intensity of the light in response to a user input applied to the brightness control slider 610. As shown in FIG. 1B, the brightness control slider 610 can also be controlled by a user manually pressing one or more brightness control switches on the device 100.

FIG. 7A illustrates that the application 602 can render a light color selection GUI 700 when a user applies a user input to the light color selection icon 612 (see FIG. 6). The light color selection GUI 700 can present the user with a variety of color options 702 for changing the colors of the lights generated by the LEDs 206. For example, the light color selection GUI 700 can give the user an option of selecting a substantially white light, red light, orange light, yellow light, green light, baby blue light, dark blue light, purple light, pink light, or a combination thereof.

The light color selection GUI 700 can also display a light color cycling icon 704 which instructs the LEDs 206 of the device 100 to cycle through a variety of light colors such that each light color is displayed for a predetermined time period.

The light color selection GUI 700 can also display a custom lighting icon 706. The custom lighting icon 706 can allow a user to remotely instruct the device 100 to display a custom light color or color combination determined by the user.

FIG. 7B illustrates that a custom color GUI 708 can be displayed when a user applies a user input to the custom lighting icon 706. As shown in FIG. 7B, an RGB color wheel 710 can be displayed as part of the custom color GUI 708 which allows a user to remotely instruct the LEDs 206 of the device 100 to display a custom light color. The custom light color can be a color not included as part of the color options 702 presented through the light color selection GUI 700. A custom color selection 712 can be displayed through a window graphic or a circular graphic which informs the user of the custom color selected.

FIGS. 7A and 7B illustrate that the device 100 can be used or function as a remote controlled nightlight when a user, such as a parent of a child, places the device 100 in a room of the child and runs the application 602 on the client device 400 in order to select a lighting color that soothes the child or relieves the child of fear or anxiety concerning the darkness. As shown in FIG. 1B, a user can also manually turn on the LEDs 206 by manually pressing the on/off switch 124 and adjusting the brightness of the LEDs 206 by pressing the one or more brightness control switches 128.

Figure 8:
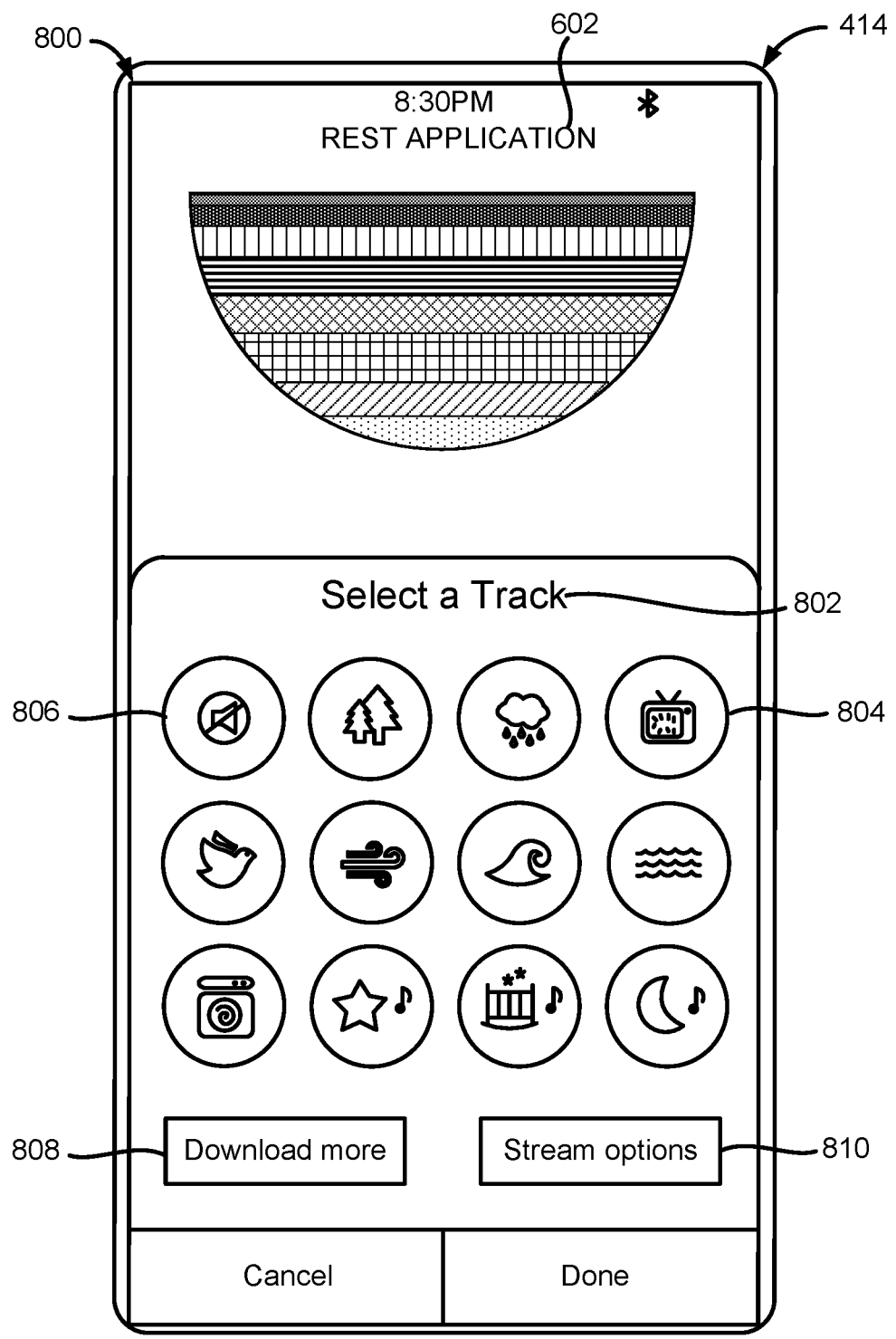
FIG. 8 illustrates another example GUI of an application running on a client device configured to control the sleep training device.

FIG. 8 illustrates that the application 602 can render a sound selection GUI 800. The application 602 can display or render the sound selection GUI 800 when a user applies a user input to the sound selection icon 614 (see FIG. 6). The sound selection GUI 800 can present the user with a variety of sound options 802 generated by the one or more speakers 204. For example, the sound options 802 can include a nature sound, a falling rain sound, a static white-noise sound, a bird chirp sound, a wind-blowing sound, an ocean wave sound, a babbling brook sound, a laundry machine sound, one or more pre-recorded tunes (e.g., a pre-recorded lullaby), or a combination thereof. The sound options 802 can be displayed or presented to a user through a number of sound selection buttons 804. Each of the sound selection buttons 804 can have a graphic specially designed to associate a particular sound option 802 with the particular sound selection button 804. The sound selection GUI 800 can also present or display a mute button 806 configured to instruct the audio component 202 of the device 100 to stop generating any type of sounds.

FIG. 8 illustrates that the device 100 can be used or function as a remote controlled noise machine or noise maker such as a white-noise machine. For example, a parent of a child can place the device 100 in a room of the child and run the application 602 remotely on the client device 400 in order to play a sound or tune that soothes the child or assists the child in going to sleep. As shown in FIG. 1B, a user can also manually turn on the device 100 to generate a sound by manually pressing the on/off switch 124 and then the play button 130. The user can also manually select amongst different sound options 802 pressing the track selection buttons 132 or control the volume by pressing the volume control switches 126.

FIG. 8 also illustrates that the application 602 can provide a download option 808 to download additional sounds or tunes to supplement or update the currently stored sounds or tunes. The additional sounds or tunes can be downloaded via WiFi (that is, received over WiFi from the server 416) or directly from the client device 400 via Bluetooth®. The additional sounds or tunes can be stored in the system memory 501, on a memory card (e.g., a Secure Digital (SD) card) within the memory card slot 134, or a combination thereof. The additional sounds or tunes can also be downloaded into the system memory 501 from a memory card inserted into the memory card slot 134. The sound selection GUI 800 can also be updated such that each new sound or tune has an associated sound selection button 804. The application 602 can also provide a stream option 810 to stream new sounds via WiFi.

Figure 9:
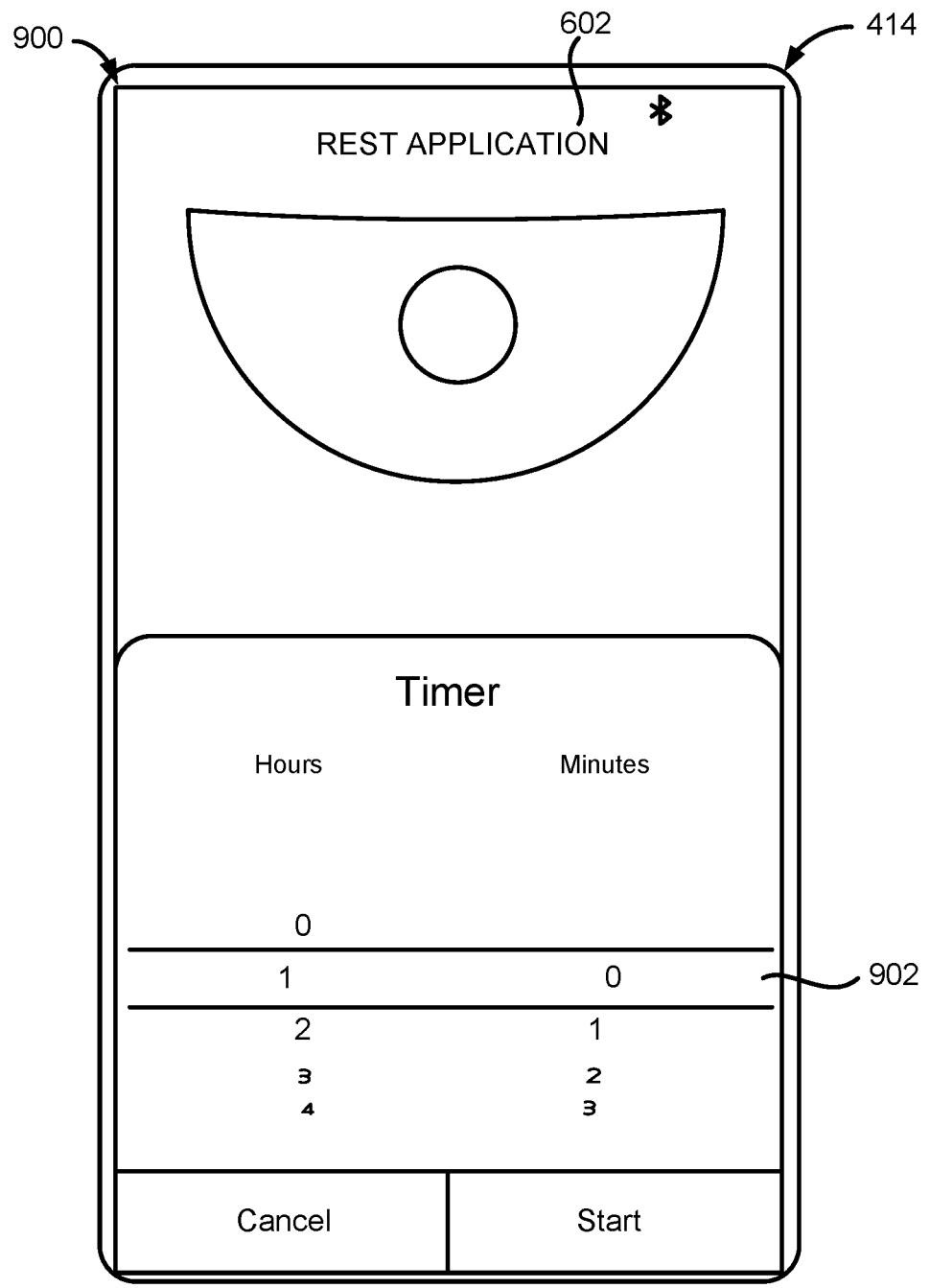
FIG. 9 illustrates another example GUI of an application running on a client device configured to control the sleep training device.

FIG. 9 illustrates that the application 602 can render a timer GUI 900. The application 602 can display or render the timer GUI 900 when a user applies a user input to the timer icon 616 (see FIG. 6). The timer GUI 900 can present the user with a countdown time scroll picker 902. After a user selects a desired amount of time by applying a user input to the countdown time scroll picker 902, the timer GUI 900 will display a countdown timer indicating the amount of time remaining. When the amount of time remaining on the countdown timer has elapsed, the device 100 powers off or deactivates. In this manner, the device 100 can be used or function as a remote controlled nightlight or noise machine having a timer function.

FIG. 10A-10D illustrates that the application 602 can render a number of sleep program GUIs 1000. The application 602 can display or render the sleep program GUIs 1000 when a user applies a user input to the program icon 618 (see FIG. 6). The sleep program GUIs 1000 can allow a user to set or schedule one or more sleep programs 1002. The sleep programs 1002 can dictate when and for how long the device 100 can automatically generate one or more lights or sounds. The sleep programs 1002 can be scheduled based on a number of set parameters including a program start time 1010, a program end time or duration 1012, a program frequency 1014 or start date(s), or a combination thereof.

As shown in FIG. 10A, the application 602 can display a number of sleep programs 1002 simultaneously. Each of the sleep programs 1002 can be saved or stored in a client memory 406 of the client device 400, a system memory 501 of the device 100, in one or more databases accessible to the one or more servers 416, or a combination thereof. A user can schedule or enable any of the previously stored or saved sleep programs 1002 using toggle buttons 1005 displayed as part of the sleep program GUIs 1000. The client device 400 can transmit or send the sleep programs 1002 set by the user to the device 100 via the server 416 through WiFi, via a short-range wireless communication protocol 402, or a combination thereof. The sleep programs 1002 can be stored in the system memory 502 of the device 100 when received by the device 100. The device 100 can initiate a sleep program 1002 when one or more set parameters (e.g., a program start time 1010, a start date, etc.) associated with the sleep program 1002 are met.

At least one of the sleep programs 1002 can be a time-to-rise program 1006. The time-to-rise program 1006 can include one or more instructions to have the device 100 generate a light of a certain color from the LEDs 206 for a specific period of time without sound. The purpose of the time-to-rise program 1006 can be to inform a child when it is permissible to leave a child's room or wake up other members of the child's household. In addition to the time-to-rise program 1006, a user can set or schedule a naptime program, a bedtime program, an audio alarm program, a visual alarm program, or a combination thereof. The sleep programs 1002 can promote healthy and routine sleep habits that benefit a child's development and general well-being.

As shown in FIGS. 10A-10D, a user can apply a user input to an add program icon 618 to add a new program. The user can input a program name 1008 through the sleep program GUI 1000 as well as schedule a program start time 1010, a program duration 1012, and a program frequency 1014. FIG. 10B also illustrates that the user can also set a program volume 1016, a program light brightness 1018, or a combination thereof through the sleep program GUIs 1000.

FIGS. 10A-10D illustrate that the device 100 can be used or function as a programmable or remote-controllable alarm clock or a programmable or remote-controllable time-to-rise light. In all such instances, a user can also customize the volume of sounds or the brightness of lights to be generated by the device 100 at a specific time and for a specific duration. As will be discussed in more detail in the following sections, a user can also enable a lock function 1300 (see FIG. 13) as part of any sleep program 1002.

Figure 11:
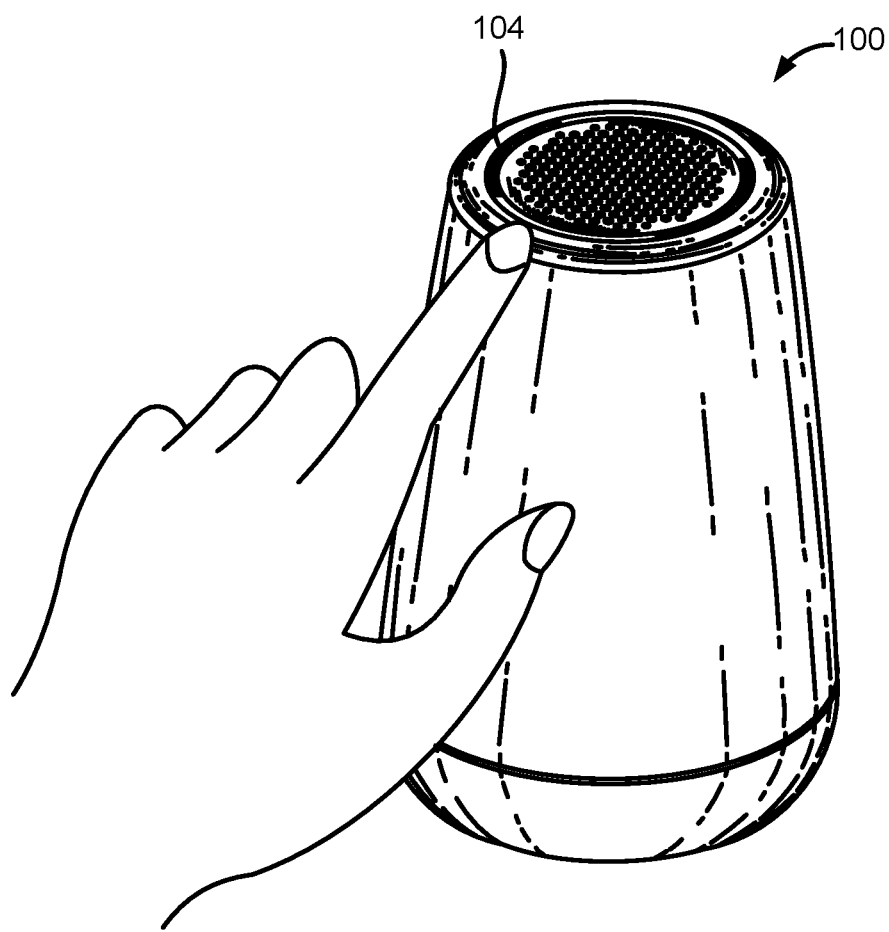
FIG. 11 illustrates a user touching a capacitive touch component configured to control the sleep training device.

FIG. 11 illustrates that a user can physically contact the capacitive touch component 104 to power on or activate the device 100. In addition, a user can also cycle through one or more preset favorite settings 1206 (see FIG. 12B) by continuously touching or making physical contact with the capacitive touch component 104. Although the capacitive touch component 104 is shown as a component at the top 108 of the device 100, it is contemplated by this disclosure that the capacitive touch component 104 can also be positioned along a side of the device 100 or along the housing base 112.

Figure 12A:
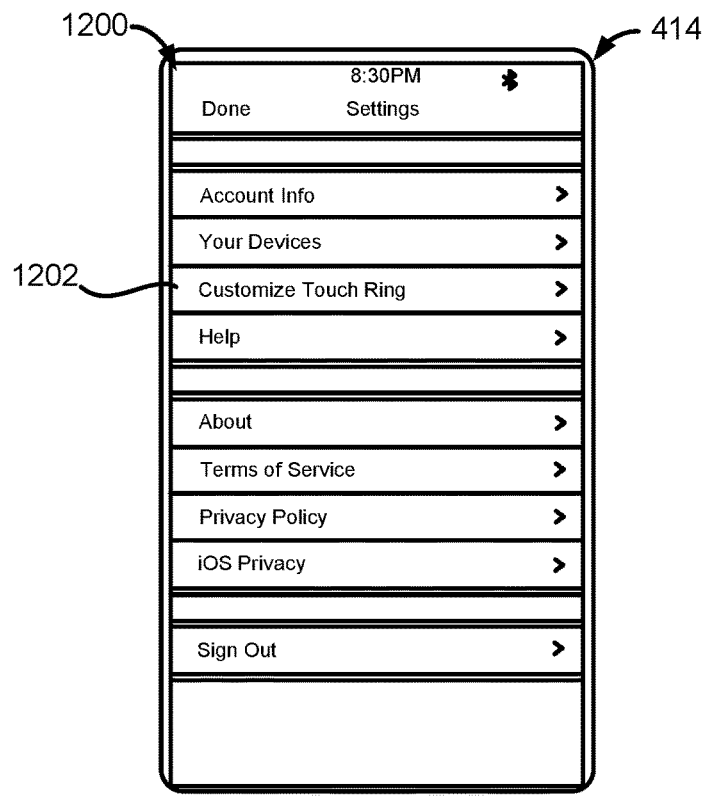
FIGS. 12A-12B illustrate other example GUIs of an application running on a client device configured to control the sleep training device.

FIG. 12A illustrates that the application 602 can render a settings GUI 1200. The application 602 can display or render the settings GUI 1200 in response to a user applying a user input to the settings icon 606 (see FIG. 6). The user can make certain changes to an account of the user or a device setting through the settings GUI 1200. FIG. 12A also illustrates that the settings GUI 1200 can include a ring customization button 1202 or selector.

Figure 12B:
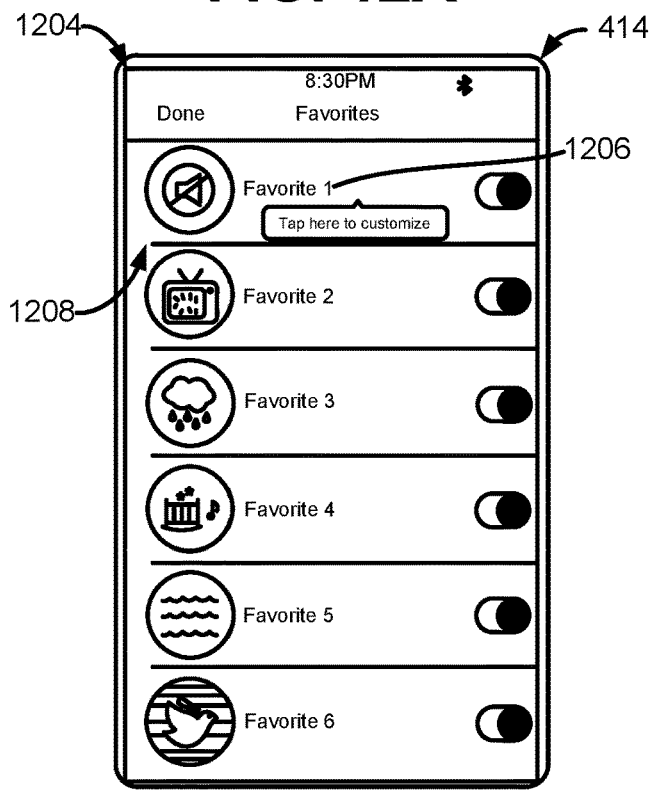

FIG. 12B illustrates that the application 602 can render a ring customization GUI 1204 in response to a user applying a user input to the ring customization button 1202 or selector. The ring customization GUI 1204 can allow a user to set a number of favorite settings 1206 including a particular light color and/or a particular sound generated by the device 100. FIG. 12B also illustrates that the user can adjust a favorite settings sequence 1208 such that the device 100 cycles through the favorite settings 1206 in a particular order or sequence in response to repeated or consecutive user contacts with the capacitive touch component 104. The application 602 can store multiple favorite settings 1206 on the client device 400, on one or more servers 416, or a combination thereof. A user can initiate any of the previously stored or saved favorite settings 1206 using toggle buttons displayed as part of the ring customization GUI 1204.

Figure 13:
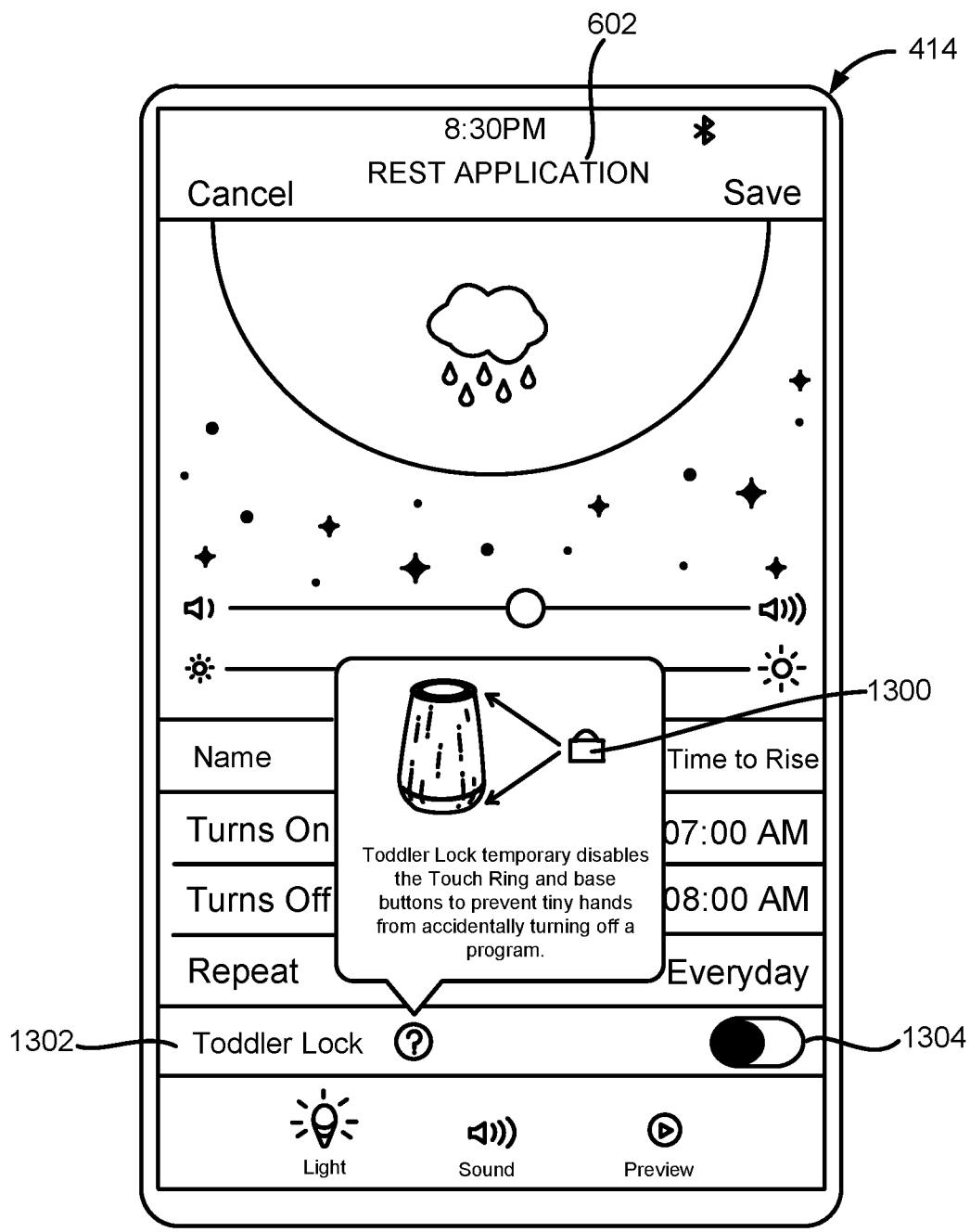
FIG. 13 another example GUI of an application running on a client device configured to control the sleep training device.

FIG. 13 illustrates that the application 602 can also provide a lock function 1300. The lock function 1300 can be provided as part of one or more sleep program GUIs 1000. The lock function 1300 can allow a user of the client device 400 to lock the device 100 when one or more sleep programs 1002 are in operation or have been initiated. The device 100 can be programmed to execute certain instructions to lock the device 100 such that a child or another user cannot disable a sleep program 1002 (such as a time-to-rise program 1006 or a naptime program) or a sound and/or light currently generated by the device 100 using the physical switches 106 or the capacitive touch component 104 of the device 100. When the device 100 is locked, the physical switches 106, the capacitive touch component 104, or a combination thereof cannot be disabled or deactivated until the sleep program 1002 concludes or is terminated. For example, the system processor 502 of the device 100 can execute instructions stored in the system memory 501 to temporarily disable or deactivate at least one of the physical switches 106, the capacitive touch component 104, or a combination thereof when the sleep program 1002 has been initiated.

The lock function 1300 can be enabled when a user applies a user input to a lock toggle 1304 displayed as part of a lock user interface 1302 of the sleep program GUI 1000. The client device 400 can transmit a lock instruction from the client device 400 to the device 100 directly or to the server 416 upon a user applying a user input to the lock toggle 1304. The client device 400 can transmit the lock instruction from the client device 400 to the device 100 or the server 416 via the antenna 508 and the communication unit processor 500. Once the device 100 has received the lock instruction from the client device 400 or the server 416, the system processor 502 can disable at least one of the physical switches 106, the capacitive touch component 104, or a combination thereof such that any electrical signals received in response to the actuation of such switches or components are ignored or not processed by the system processor 502.

Alternatively, the lock function 1300 can be provided as part of a standalone lock user interface 1302 or as part of the timer GUI 900, the sound selection GUI 800, the light color selection GUI 700, or a combination thereof. The lock function 1300 can allow a user of the client device 400 to lock the device 100 even when no sleep programs 1002 have been initiated or are in operation. The device 100 can be programmed to execute certain instructions to lock the device 100 such that a child or another user cannot disable a sound and/or light currently generated by the device 100 using the physical switches 106 or the capacitive touch component 104 of the device 100. The client device 400 can transmit a lock instruction from the client device 400 to the device 100 directly or to the server 416 upon a user applying a user input to the lock toggle 1304. The client device 400 can transmit the lock instruction from the client device 400 to the device 100 or the server 416 via the antenna 508 and the communication unit processor 500. Once the device 100 has received the lock instruction from the client device 400 or the server 416, the system processor 502 can disable at least one of the physical switches 106, the capacitive touch component 104, or a combination thereof such that any electrical signals received in response to the actuation of such switches or components are ignored or not processed by the system processor 502. When the device 100 is locked, the physical switches 106, the capacitive touch component 104, or a combination thereof cannot be disabled or deactivated until the user applies another user input to the lock toggle 1304 to unlock the device 100.

In some variations, a user can disable the lock function 1300 by manually pressing or actuating one or more physical switches 106, the capacitive touch component 104, or a combination thereof in a certain sequence, for a certain duration, or both. For example, a user can disable the lock function 1300 set remotely by the client device 400 by manually pressing both volume control switches 126 at the same time or manually pressing the play button 130 first for three seconds and then pressing one of the tracking selection buttons 132. It should be understood by one of ordinary skill in the art that other button combinations can also be used to unlock the lock function 1300. Such button unlock combinations can be stored as part of the firmware of the device 100 in the system memory 501. Moreover, the button unlock combinations can also be updated as part of a device firmware update.

Figure 14:
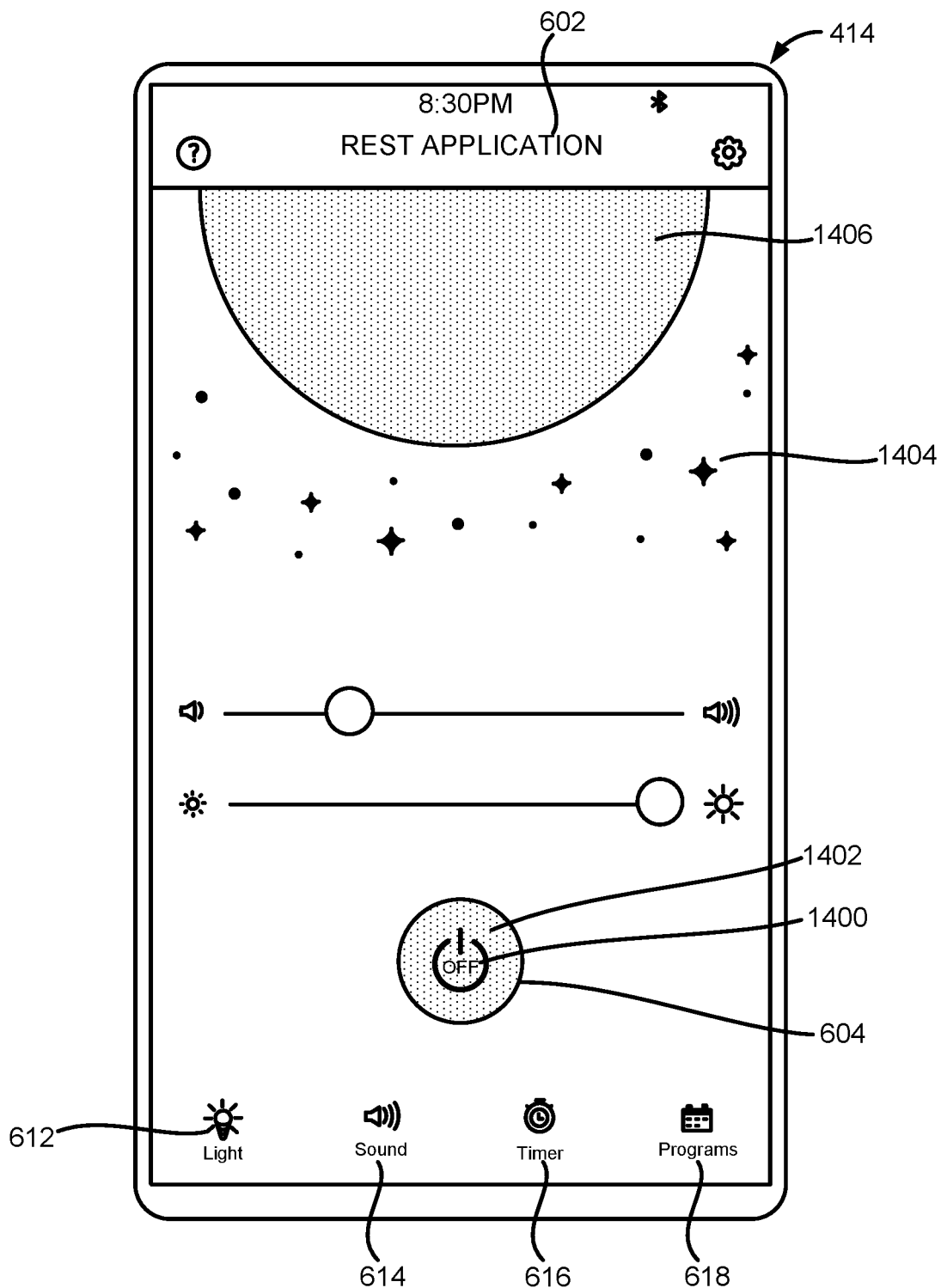
FIG. 14 illustrates another example GUI of an application running on a client device configured to control the sleep training device.

FIG. 14 illustrates that the client device 400 can be used to shut off, power off, or deactivate the device 100 when a user applies a user input to the on/off button 604 displayed through any of the GUIs of the application 602. For example, the on/off button 604 can be displayed whenever the device 100 is running a sleep program 1002 or counting down from a timer. As shown in FIG. 14, one or more graphic properties of the on/off button 604 can change when the device 100 is powered off or deactivated. For example, the on/off button 604 can display a text message 1400 or change a button color 1402 when the device 100 is powered off or deactivated. One or more graphic properties of the application 602 such as a color of an application background 1404 or an application graphic 1406 can change or a brightness of one or more application graphics 1406 or backgrounds can change when the device 100 is powered off or deactivated. Moreover, as shown in FIG. 1B, the device 100 can also be powered off or deactivated when a user manually presses the on/off switch 124. The same changes to the application background 1404, the application graphic 1406, the button color 1402, the text message 1400 displayed on the on/off button 604, or a combination thereof can also be made when a user manually presses the on/off switch 124 on the device 100. For example, the application background 1404 or the button color 1402 of the on/off button 604 can dim or darken on an application GUI displayed on the client device 400 when a user manually presses the on/off switch 124 on the device 100 to power off the device 100. These changes to the GUI of the application 602 can inform a user of the client device 400 that the device 100 has been manually powered off or deactivated (by the same user, a child, or another user) if the client device 400 is remote from the device 100 or outside a room or space where the device 100 is currently residing. One benefit of this feature is allowing a user of the client device 400 to know or remember when the device 100 has been powered off or turned off by the same user, another user, or a child in the same room as the device 100.

Figure 15:
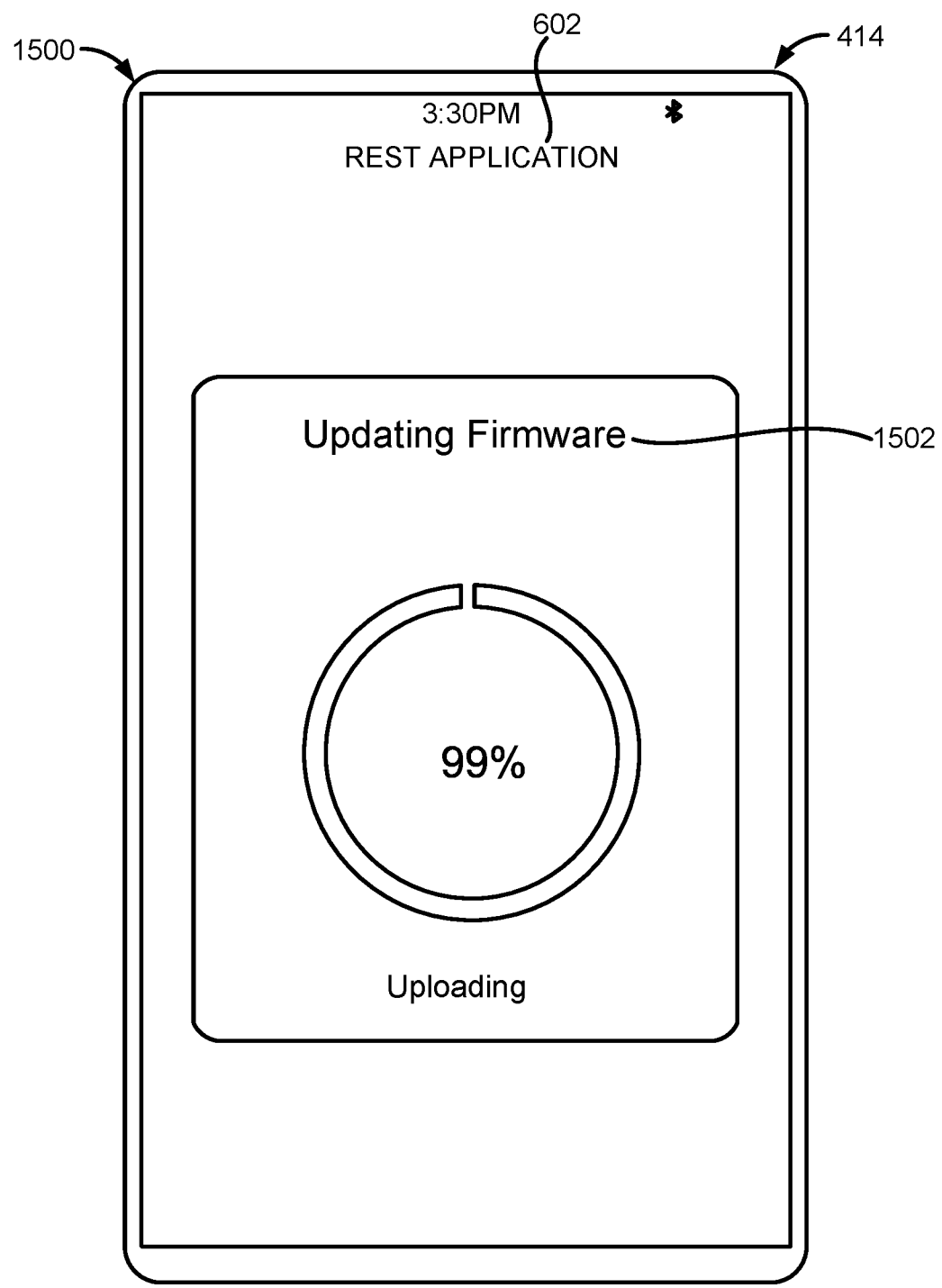
FIG. 15 illustrates another example GUI of an application running on a client device configured to control the sleep training device.

FIG. 15 illustrates that the application 602 can render a firmware update GUI 1500 to inform a user that the firmware 1502 of the device 100 is being updated. The firmware 1502 of the device 100 can be updated when a user runs the application 602 on a client device 400 within wireless communication range of the device 100. Updates to the firmware 1502 can be pushed to the device 100 via the client device 400 periodically to improve the functioning of the device 100 or introduce new device features.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

We claim:

1. A sleep training device, comprising:
   a printed circuit board (PCB) comprising a processor, a real-time clock integrated circuit (IC), a memory, and a wireless communication unit;
   an audio component electrically coupled to the processor;
   light-emitting diodes (LEDs) electrically coupled to the processor;
   a capacitive touch component electrically coupled to the processor;
   physical switches electrically coupled to the processor, wherein the physical switches are configured to control at least one of the LEDs and the audio component;
   a device housing configured to house the PCB, the audio component, the LEDs, and at least part of the physical switches; and
   wherein the processor is programmed to execute instructions stored in the memory to:
      receive instructions to schedule a sleep program from a server communicatively coupled to the sleep training device after the sleep program is set by a client device communicatively coupled to the server, and wherein the sleep program comprises instructions to disable at least one of the physical switches and the capacitive touch component when the sleep program is initiated in response to a set parameter associated with the sleep program being met, and
      disable at least one of the physical switches and the capacitive touch component when the sleep program is initiated.

2. The device of claim 1, wherein the device housing comprises a housing base, a device top, and a light diffusing cover, wherein the housing base comprises a device bottom, wherein the device housing converges in size from the housing base to the device top to enhance a stability of the sleep training device, wherein the device bottom is wider than the device top, and wherein the physical switches are located along the device bottom.

3. The device of claim 2, wherein the PCB is housed within the housing base, wherein the housing base is acetabular or bowl-shaped.

4. The device of claim 2, wherein the light diffusing cover comprises a polymeric material configured to diffuse light and dissipate heat generated by the LEDs.

5. The device of claim 4, further comprising a cylindrical support column having an enclosed outer surface extending upward from the housing base, wherein the support column is configured to support at least part of the audio component and house one or more electrical components and wires, and wherein the support column is covered by an opaque material such that the one or more electrical components and wires within the support column do not cast shadows from light generated by the LEDs.

6. The device of claim 5, wherein the LEDs are arranged in a circular pattern surrounding the support column at a base of the support column.

7. The device of claim 1, wherein the LEDs are RGBW LEDs.

8. The device of claim 1, wherein the audio component comprises a speaker coupled to an amplifier, and wherein the amplifier is electrically coupled to the processor.

9. The device of claim 8, further comprising a covering plate configured to cover a top of the device housing and positioned above the speaker.

10. The device of claim 1, further comprising one or more rechargeable batteries configured to supply power to at least one of the processor, the real-time clock IC, the memory, the wireless communication unit, the audio component, the LEDs, and the physical switches, wherein the one or more rechargeable batteries are housed within the support column.

11. The device of claim 1, wherein the wireless communication unit is a wireless fidelity (WiFi) communication unit.

12. The device of claim 1, further comprising a gesture control sensor electrically coupled to the processor, wherein the gesture control sensor is configured to detect a hand gesture made by a user in a vicinity of the gesture control sensor.

13. The device of claim 1, further comprising a Bluetooth® audio interface electrically coupled to the processor.

14. The sleep training device of claim 1, wherein the processor is programmed execute further instructions to re-enable or re-activate at least one of the physical switches and the capacitive touch component in response to a user applying a user input to a mobile application running on the client device.

15. The sleep training device of claim 1, wherein the instructions to disable at least one of the physical switches and the capacitive touch component are included as part of the sleep program in response to a user applying a user input to a lock toggle graphic displayed as part of a mobile application running on the client device.

16. The sleep training device of claim 15, wherein the lock toggle graphic is included as part of a sleep program graphical user interface (GUI) presented as part of the mobile application running on the client device, wherein the sleep program GUI is used by the user to set the sleep program.

17. The sleep training device of claim 1, wherein the processor is programmed to execute instructions to play a sound via the audio component when the sleep program is initiated, wherein the sound is set by the client device communicatively coupled to the server.

18. The sleep training device of claim 1, wherein the sleep training device is configured to be powered on in response to a user input applied to the capacitive touch component.

19. A sleep training device, comprising:
- a printed circuit board (PCB) comprising a processor, a real-time clock integrated circuit (IC), a memory, and a wireless communication unit;
- a capacitive touch component electrically coupled to the processor;
- an audio component electrically coupled to the processor;
- light-emitting diodes (LEDs) electrically coupled to the processor;
- physical switches electrically coupled to the processor, wherein the physical switches are configured to control at least one of the LEDs and the audio component;
- a device housing configured to house the PCB, the audio component, the LEDs, and at least part of the physical switches and the capacitive touch component, wherein at least part of the capacitive touch component is exposed by the device housing, and wherein the device housing comprises a housing base and a light diffusing cover; and
- a cylindrical support column having an enclosed outer surface extending upward from the housing base, wherein the support column is configured to support at least part of the audio component and house one or more electrical components and wires, and wherein the support column is covered by an opaque material such that the one or more electrical components and wires within the support column do not cast shadows from light generated by the LEDs, and
- wherein the processor is programmed to execute instructions stored in the memory to disable at least one of the physical switches and the capacitive touch component when a sleep program stored in the memory is initiated in response to a set parameter associated with the sleep program being met.

20. The device of claim 19, wherein the capacitive touch component comprises an annular ring and wherein the annular ring is made of an electrically-conductive material, and wherein the sleep training device is configured to be powered on in response to a user input applied to the capacitive touch component.

21. The device of claim 19, wherein the PCB is housed within the housing base.

22. The device of claim 19, wherein the light diffusing cover comprises a polymeric material configured to diffuse light and dissipate heat generated by the LEDs.

23. The device of claim 19, wherein the LEDs are arranged in a circular pattern surrounding the support column at a base of the support column.

24. The device of claim 19, wherein the LEDs are RGBW LEDs.

25. The device of claim 19, wherein the audio component comprises a speaker coupled to an amplifier, and wherein the amplifier is electrically coupled to the processor, wherein the processor is programmed to execute instructions to play a sound via the audio component when the sleep program is initiated.

26. The device of claim 25, further comprising a covering plate configured to cover a top of the device housing and positioned above the speaker.

27. The device of claim 19, wherein the wireless communication unit is a wireless fidelity (WiFi) communication unit.

28. The device of claim 19, wherein the instructions to disable at least one of the physical switches and the capacitive touch component are included as part of the sleep program in response to a user applying a user input to a lock toggle graphic displayed as part of a mobile application running on the client device.

29. The device of claim 19, further comprising a gesture control sensor electrically coupled to the processor, wherein the gesture control sensor is configured to detect a hand gesture made by a user in a vicinity of the gesture control sensor.

30. A method of operating a sleep training device, comprising:
- receiving an instruction to schedule a sleep program from a server communicatively coupled to the sleep training device after the sleep program is set by a client device communicatively coupled to the server, wherein the sleep training device further comprises:
  - a printed circuit board (PCB), comprising a processor, a real-time clock integrated circuit (IC), a memory, and a wireless communication unit,
  - an audio component electrically coupled to the processor,
  - light-emitting diodes (LEDs) electrically coupled to the processor,
  - a capacitive touch component electrically coupled to the processor,
  - a number of physical switches electrically coupled to the processor, wherein the physical switches are configured to control at least one of the LEDs and the audio component, and
  - a device housing configured to house the PCB, the audio component, the LEDs, and at least part of the physical switches;
- initiating, using the processor, the sleep program once a set parameter associated with the sleep program is met; and
- disabling at least one of the physical switches and the capacitive touch component when the sleep program is initiated, wherein the sleep program comprises instructions to disable at least one of the physical switches and the capacitive touch component when the sleep program is initiated.

31. The method of claim 30 wherein the sleep training device is configured to be powered on in response to a user input applied to the capacitive touch component.

32. The method of claim 30, wherein the device housing comprises a housing base, a device top, and a light diffusing cover, wherein the housing base comprises a device bottom, wherein the device housing converges in size from the housing base to the device top to enhance a stability of the sleep training device, wherein the device bottom is wider than the device top, and wherein the physical switches are located along the device bottom.

33. The method of claim 32, wherein the light diffusing cover comprises a polymeric material configured to diffuse light and dissipate heat generated by the LEDs.

34. The method of claim 33, wherein the sleep training device further comprises a cylindrical support column having an enclosed outer surface extending upward from the housing base, wherein the support column is configured to support at least part of the audio component and house one or more electrical components and wires, and wherein the support column is covered by an opaque material such that the one or more electrical components and wires within the support column do not cast shadows from light generated by the LEDs.

35. The method of claim 34, wherein the LEDs are arranged in a circular pattern surrounding the support column at a base of the support column.

36. The method of claim 30, wherein the LEDs are RGBW LEDs.

37. The method of claim 30, wherein the audio component comprises a speaker coupled to an amplifier, and wherein the amplifier is electrically coupled to the processor, and wherein the method further comprises playing a sound via the audio component when the sleep program is initiated.

38. The method of claim 30, wherein the wireless communication unit is a wireless fidelity (WiFi) communication unit.

39. The method of claim 30, wherein the sleep training device further comprises a gesture control sensor electrically coupled to the processor, wherein the gesture control sensor detects a hand gesture made by a user in a vicinity of the gesture control sensor.

40. The method of claim 30, further comprising re-enabling or re-activating at least one of the physical switches and the capacitive touch component in response to a user applying a user input to a mobile application running on the client device.

41. The method of claim 30, wherein the instructions to disable at least one of the physical switches and the capacitive touch component are included as part of the sleep program in response to a user applying a user input to a lock toggle graphic displayed as part of a mobile application running on the client device.

42. The method of claim 41, wherein the lock toggle graphic is included as part of a sleep program graphical user interface (GUI) presented as part of the mobile application running on the client device, wherein the sleep program GUI is used by the user to set the sleep program.

\* \* \* \* \*